United States Patent [19]
Akiyoshi et al.

[11] Patent Number: 5,537,206
[45] Date of Patent: Jul. 16, 1996

[54] METHOD FOR ANALYZING STEEL AND APPARATUS THEREFOR

[75] Inventors: Takanori Akiyoshi; Tadashi Mochizuki; Akiko Sakashita; Yohichi Ishibashi; Satoshi Kinoshiro; Yoshihito Iwata; Yoshihiko Kawai; Yoichi Nimura; Hiroaki Miyahara, all of Kawasaki, Japan

[73] Assignee: NKK Corporation, Tokyo, Japan

[21] Appl. No.: 331,792

[22] Filed: Oct. 31, 1994

[30] Foreign Application Priority Data

Nov. 2, 1993 [JP] Japan ................................. 5-274590
Dec. 10, 1993 [JP] Japan ................................. 5-309975

[51] Int. Cl.$^6$ ............................ G01N 1/00; G01N 21/63; G01N 21/72; G01N 21/73
[52] U.S. Cl. ........................... 356/315; 356/36; 356/316; 356/318
[58] Field of Search ............................. 356/36, 313, 315, 356/316, 318

[56] References Cited

U.S. PATENT DOCUMENTS

| 3,602,595 | 8/1971 | Dahlquist et al. | 356/36 |
| 3,791,743 | 2/1974 | Cody et al. | 356/313 |
| 4,598,577 | 7/1986 | Jowitt et al. | 356/36 |
| 4,615,225 | 10/1986 | Sainz | 356/36 |

FOREIGN PATENT DOCUMENTS

| 62-14773 | 4/1987 | Japan. |
| 3-167446 | 7/1991 | Japan. |

OTHER PUBLICATIONS

JIS G 1253, "Method for Photoelectric Emission Spectrochemical Analysis of Iron and Steel". 1983.
Kantor et al., "Atomic–Absorption Spectrometry of Laser–Nebulized Sample", Talanta, Vol. 23, No. 8, Aug. 1976, pp. 585–586.
Mitchell et al, "Direct Determination of Copper in Solids by Direct Current Argon Plasma Emission Spectrometry with Sample Introduction Using Laser Ablation", Applied Spectroscopy, Vol. 41, No. 1, 1987, pp. 141–148.

*Primary Examiner*—F. L. Evans
*Attorney, Agent, or Firm*—Frishauf, Holtz, Goodman, Langer & Chick

[57] ABSTRACT

A method for analyzing steel which comprises: grinding an analysis area of a steel ingot; sealing the analysis area with a sealing section of a cell for generating fine particles; again grinding the analysis area, while an argon gas is introduced into the cell; irradiating a pulsed laser beam of $10^8$ W/cm$^2$ or more onto the analysis area at an irradiating spot of at least 1 mm$^2$ to generate the fine particles; moving the irradiating spot; and transferring the generated fine particles by the argon gas to a plasma emission analysis for analysis. A further method for analyzing steel comprises: solidifying a molten steel sample, forming a red-hot sample; putting the sample into a sample holding section of a sample chamber under a purified argon gas atmosphere, the sample holding section having an inner curved surface the same as a curved surface of the sample; irradiating a pulsed laser onto the sample to remove a sample surface layer of 25 μm or more of the sample and to generate fine particles from the sample; and exciting the fine particles by a plasma emission analyzer to analyze the composition of the fine particles.

31 Claims, 12 Drawing Sheets

METHOD FOR ANALYZING STEEL AND APPARATUS THEREFOR

BACKGROUND OF THE INVENTION

1. Field of the Invention

The present invention relates to a method for analyzing a chemical compositions of steel and a method therefor.

2. Description of Related Arts

The Composition of a steel significantly affects properties of the steel, and the composition analysis is indispensable for quality control. The oxygen blowing period in the steel making process is so short as to be about 15 minutes. At the final stage of the oxygen blowing, the composition of the molten steel is analyzed to feed back the analyzed data for controlling the composition and the temperature of the molten steel to be within a predetermined range. Therefore, a rapidity of magnitude of seconds is required for the analysis. Further, the characteristics of the steel vary with its composition and heat treatment. Based on the identified composition of the molten steel, strict conditions of heat treatment for the composition of the steel are set to produce a steel having uniform characteristics.

In the conventional method of the analysis, the main stream of analysis for a steel was an emission spectral analysis using a discharge excitation of spark or arc, which is specified in JIS-G-1253. According to the method, the spectra is obtained only after passing the discharged and emitted light through a slit, so the discharge point has to be fixed. As a result, a specimen for analysis is required to be set at a fixed discharge point. In addition, this method requires the discharge point on the specimen to be finished to a smooth and flat surface for procuring a sufficient analytical accuracy. To satisfy these conditions, the conventional method needed to cut off a small ingot of necessary size from the target ingot and to finish the surface of the specimen to a smooth and flat face. For this reason, the pre-treatment for preparing the specimen consumed a lot of work and time. With a change of steel-making technology, however, the importance of a rapid analysis by skipping such a time-taking specimen preparation has been remarkably emphasized.

One of the existing methods of the rapid analysis is an spectral emission analysis in which the emission section is separated from a spectral section and the beam generated by discharge is sent to the spectral section through an optical fiber. This method contributes merely to making the discharge point relatively free. The method, however, still requires the smooth and flat surface of a specimen and the control of discharge characteristics because these characteristics are affected by the temperature of the specimen. In addition, this method has a more serious problem of transmittance of the optical fiber to be used, and the transmittance of wave length is 200 nm or less. The wave length is so extremely low that the analytical spectra of C, P, and S which are important components of steel can not transmit through the optical fiber. This disables the analysis of these elements.

The following method solved the problems of the temperature of the specimen and of the beam transmittance. The method irradiated a high density energy to vaporize a part of a mother specimen and to collect the vaporized fine particles as a sample, and carried the sample of above the collected fine particles to an emission spectral analyzer with an inert gas. An equipment using plasma arc as a high density energy was disclosed in Japanese Patent Examined Publication No. 14773/87.

According to the mentioned patent publication, a large specimen is covered by a cylinder for generating fine particles provided with a plasma emission tube, and the specimen is heated by plasma arc to vaporize a part of it. A carrier gas is introduced to the cylinder, and an edge of the cylinder contacting the large specimen is maintained on a horizontal plane while the inside space of the cylinder is sealed to be air-tight. A vaporized part of the specimen becomes fine particles, which are then transferred by the carrier gas to the plasma emission spectral analyzer through the fine tube to be analyzed. The above described patent publication describes that high vaporization rate is the reason for selecting the plasma arc as an irradiating energy.

When the above described disclosed method is applied to an actual specimen, however, several problems remain. The one is that a difference of composition appears between the collected fine particle sample and the mother specimen, which hinders the acquisition of sufficient analytical accuracy and correct values.

another problem is that, when a specimen is a hot steel ingot, attention is not paid to handling the specimen taken from the hot steel ingot and the hot steel ingot cannot be analyzed.

That is to say, when the specimen is one having a smooth and clean surface, the analyzer is applicable, but if the specimen is taken from a hot steel ingot, the hot steel ingot has an oxide layer on a surface layer of the hot ingot and has an oxidation-affected zone such as a decarburization layer exists beneath the oxide layer. Since the composition of the oxidation-affected zone differs from the composition of the mother material, that zone should be removed. Nevertheless, the method does not consider the removal of that type of zone. If a plasma irradiation is applied to remove the zone, the peripheral area of the irradiated part melts. The melting of peripheral area easily induces an intermixing with the components of the mother material. Consequently, repeated irradiation never attains the same composition of the melted area with that of the mother material.

Furthermore, on a hot steel ingot before being subjected to rolling, the surface is not smooth and flat due to an existing irregularity called the "oscillation mark" which appears during continuous casting and is also due to the irregularity generated at cutting step. As a result, when a cylinder for generating fine particles having a flat cut end face is applied, the carrier gas leaks from a gap between the cylinder and the specimen, which results in a fluctuation of gas volume supplied to the plasma emission spectral analyzer. The fluctuation affects the excitation condition in the plasma flame, and degrades the accuracy of analysis.

On the other hand, the following alternative method is known. The method irradiates laser onto a lump sample in a sample chamber having an inert gas atmosphere and gasifies a part of the sample to generate fine particles. The fine paticles are then introduced to an IPC(Inductively coupled plasma) analyzer to emit beam or to be ionized. The method is hereinafter referred to as laser/IPC analysis. The accuracy of the carbon analysis of this method is in question, since the method has not been reduced to practice though the shortening of the operation period has been tried. For example, JP-A-No. 167446/91 disclosed a sample exchange unit which simplifies the mounting and dismounting of the sample to and from a sample chamber and the positioning by structuring a lower half part of the sample chamber to be able to slide. Since the method disclosed by the above mention publication represents an improvement from the standpoint of avoiding the cut and adjustment handling of the sample, the method contributed to a slight degree of the time-saving but failed to achieve a significant improvement in rapidity.

SUMMARY OF THE INVENTION

The object of the present invention is to provide a method for analyzing a steel composition rapidly with a high precision and at a high accuracy and an apparatus therefor.

To attain the object, the present invention provides a method for analyzing steel which comprises the steps of:

(a) a first grinding step of mechanically grinding a surface of a steel ingot to form an analysis area on the steel ingot;

(b) bringing a sealing section of a cell into contact with the analysis area to seal the analysis area, the cell having the sealing section at an opening end thereof;

(c) a second grinding step of further grinding the analysis area to remove soil adhered on a surface layer and an oxide layer generated in the surface layer of the steel ingot, while an inert gas introduced into an inside of the cell;

(d) charging a pulsed energy of $10^8$ W/cm$^2$ or more onto the area for analysis to generate fine particles;

(e) transferring the fine particles by using the inert gas introduced into the inside of the cell to lead an excitation flame for an excitation analysis.

Furthermore, the present invention provides an apparatus for analyzing steel comprising;

(a) first grinding means for mechanically grinding a surface of a steel ingot to form an analysis area;

(b) a cell having a sealing section at an opening end thereof, the sealing section being contact with the analysis area;

(c) the cell having a gas inlet and a gas outlet at both sides thereof, an inert gas being introduced through the gas inlet and the inert gas being discharged through the gas outlet;

(d) a second grinding means for further grinding the analysis area to remove soil adhered on a surface layer and an oxide layer generated in the surface layer of the steel ingot, while the inert gas is introduced into an inside of the cell through the gas inlet;

(e) an energy charging means for charging a pulsed energy on the analysis area to generate fine particles; and (f) an excitation analyzer for analyzing the fine particles which are transferred through the gas outlet of the cell.

Further, the present invention provides another method for analyzing steel comprising the steps;

(a) preparing a sample by sampling a molten steel and solidifying the molten steel;

(b) putting the sample into a sample chamber under an inert gas atmosphere, the sample being at a red heat state;

(c) irradiating a pulsed laser beam on a surface of the sample in the sample chamber to generate fine particles, the fine particles generated from a depth of 25 μm or more under the surface being a specimen for composition analysis;

(d) transferring the fine particles to an an inductively coupled plasma analyzer; and (e) analyzing a composition of the fine particles by the inductively coupled plasma analyzer.

And still further, the present invention provides another apparatus for analyzing steel comprising:

(a) a sample chamber for a sample, the sample chamber comprising an analytical cell section, a sample holding section and an exposure hole for connecting the sample holding section with the analytical cell section, the sample being received in the sample holding section;

(b) the sample holding section having an inner surface in contact with a surface of the sample and the inner surface having a substantially same curved surface as that of the sample;

(c) a laser oscillator for irradiating a pulsed laser beam to generate fine particles, the pulsed laser beam being irradiated on the sample through the analytical cell section and the exposure hole;

(d) transfer means for transferring the fine particles to an outside of the analytical cell section by introducing an inert gas into the analytical cell section; and (e) an inductively coupled plasma analyzer for analyzing a composition of the transferred fine particles.

furthermore, the present invention provides another method for analyzing steel comprising:

irradiating a pulsed laser beam along a line on a surface of steel to generate fine particles;

transferring the generated fine particles to a detector by inert gas;

analyzing a composition of the fine particles by the detector, a transition of the composition along the line being gained and an abnormal zone of the steel being detected by the transition of the composition.

DESCRIPTION OF EMBODIMENTS

EMBODIMENT-1

Figure 1:
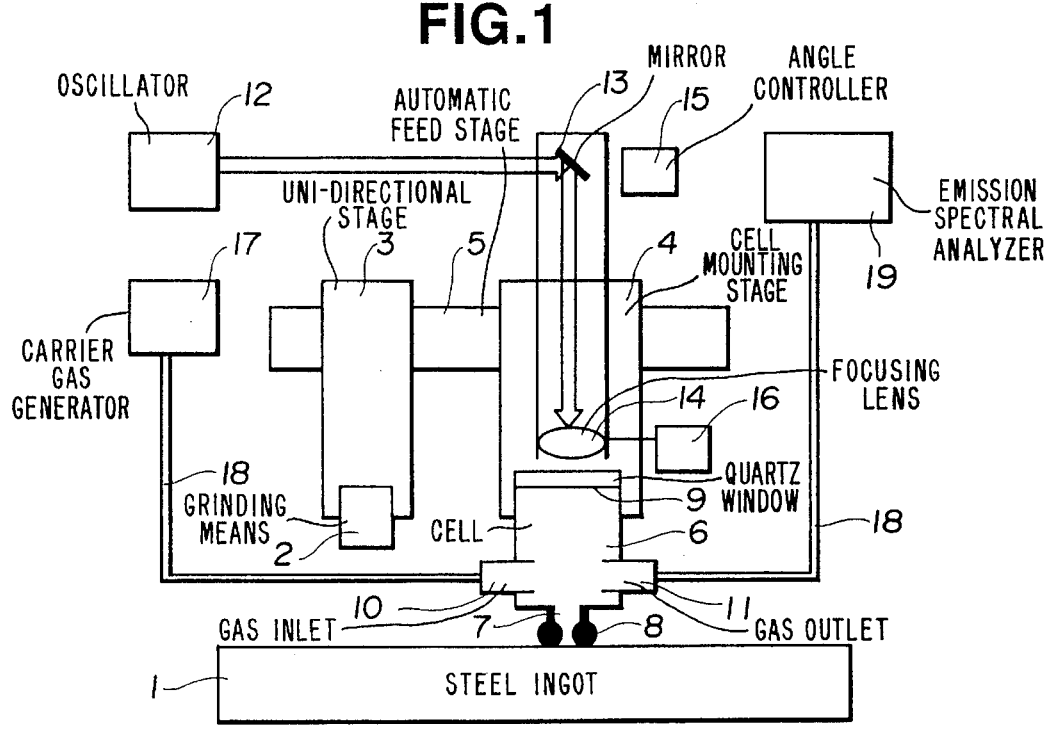
FIG. 1 is a schematic view illustrating an apparatus for analyzing steel according to an Embodiment-1 of the present invention.

If a composition of collected fine particle sample is not the same with that of a mother specimen (hereinafter referred to as "mother specimen representativeness"), an analytical accuracy is not improved even when an excitation analysis technology is improved. This phenomenon comes from a fundamental difference from an aliquot solution sample which is sampled after disolving the mother specimen, and the mother specimen representativeness is a problem unavoidably accompanied with a solid sample analysis.

One of causes to degrade the representativeness of a fine particle sample is to collect a substance which has no relation with the mother specimen along with a part of the mother specimen. One of the most often encountered phenomena is to collect a soil adhered on a surface of the mother specimen and an oxide layer formed on a surface layer of the mother specimen. The oxidizing reaction chamges a composition. For example, decarburization lowers the carbon content of the surface layer, and the degree of carbon content reduction is enhanced with an increase of temperature of the specimen.

To avoid the effect of soil and the composition change, firstly a part of mother specimen of steel ingot, where the analysis is conducted, is ground to remove the layer having a different composition from the mother specimen (hereinafter referred to as "different layer").

The present invention employs two-step grinding. One object of the grinding is to remove a layer having different composition described above, and another object of the grinding is to prepare a shape of the surface for specimen collection. The reason why a first grinding step is carried out mechanically is to place the preparation of surface shape as the first priority. The removal of the different layer can be done also in a second grinding step. Accordingly, the first grinding step is conducted responding to a surface shape of the analytical zone, and, if the surface is acceptably flat for the analysis, then the first grinding step can be omitted. When an analytical zone on the steel ingot is determined, the mechanical grinding is automatically performed by a unit for grinding the steel ingot surface which is guided by the positioning device of the grinding unit. The mechanical grinding would easily flatten the surface or remove the different layer without diffusing the different layer into a deep zone of the mother material. Since the mechanical grinding is carried out in air, the mechanical grinding is suitable for practical application.

After the mechanical grinding, the ground surface is introduced into a cell for generating fine particles. This action is for conducting the second grinding step under an inert gas atmosphere and for transferring the sufficiently cleaned surface to the succeeding sample collection step. The cell for generating the fine particles has an opening, and an edge of the opening has a sealing section. The sealing section is attached to the steel ingot to seal the steel ingot air-tightly. For a cold steel ingot, the sealing material can be a rubber "0" ring. For a hot steel ingot, an elastic heat-resistant material is used.

The cell for generating with fine particles has a gas inlet, and the gas inlet connects with an inert gas generator through a gas transfer pipe to introduce the inert gas into the cell. The introduced gas makes the inside space of the cell have an inert gas atmosphere.

As described above, the first grinding step can be omitted, but the second grinding step cannot be omitted. This is because the oxide layer generated after the first grinding step cannot be left untreated. Table 1 compares a relative standard deviation between the case where the second grinding step was applied using a spark discharge on a hot steel ingot at approximately 800° C. and the case where only the first grinding step was applied and the second grinding step was not applied to the hot steel ingot. The fine particle generation was also carried out by spark discharge, and an excitation analysis was conducted by ICP.

TABLE 1

| Analyzed Component | | C | Si | Mn | P | S | Cr | Mo |
|---|---|---|---|---|---|---|---|---|
| Content (%) | | 0.20 ∫ 0.24 | 0.20 ∫ 0.22 | 1.05 ∫ 1.35 | 0.02 ∫ 0.04 | 0.01 ∫ 0.03 | 0.31 ∫ 0.35 | 0.10 ∫ 0.15 |
| Relative Standard Deviation (%) | With 2nd Step | 5 | 3 | 5 | 5 | 9 | 2 | 3 |
| | Without 2nd Step | 30 | 15 | 15 | 10 | 20 | 5 | 8 |

In the case that the second grinding step was not applied, the relative standard deviation became several times as large as that in the case that the second grinding step was applied. Particularly for C, the value difference reached 6 times as much as that of the case without the second grinding step.

As for the second grinding step, the grinding can be performed by charging a pulsed high density energy which is used for generating the fine particles in the present invention, as well as the mechanical grinding. This mode of energy includes spark discharge, DC (direct current) discharge, and pulsed laser beam. With these modes of energy, high density energy can be charged within a short time, and the element receiving the energy instantaneously gasifies to be emitted. As a result, the grinding is conduced while the temperature of the steel ingot is remained almost unchanged, and the different layer is scarcely diffused to come into the steel ingot. The plasma discharge, which is a prior art, method is difficult to apply pulsed irradiation, and the temperature of the steel ingot increases, which allows the mixing of the different layer into the ingot.

Another important cause to impair the representativeness of the fine particle sample is the problem of selective vaporization. A different element composition generally results in a different boiling point. With the same element composition, however, a different existing phase needs a different energy for vaporization. When the charge of necessary quantity of energy for generating fine particles takes a time, the heat transferring in the mother specimen broadens the temperature distribution area. For example, the vaporization area for an element with a low boiling point becomes broader than that with a high boiling point, and the content percentage of low boiling point elements in the fine particles increases than that of the mother specimen.

The trend is rapidly diminished by charging a high density energy to shift quickly the condition toward a high temperature region. For this action, a high energy density (pulse peak energy/irradiating spot area) of $10^8$ W/cm$^2$ or more is necessary. A spark discharge or pulse laser beam is suitable for this purpose, which has a mode to charge a pulse energy, imparting energy within a short time, onto a narrow area. For example, when the energy having the same wattage is charged within 1μ see, the energy density increases to an amount of million times as much as that charged in a continuous manner, and if the charging area is selected to be 0.1 mm$^2$, the energy density becomes 10 thousand times as large as that charged onto the area of 1 cm$^2$. A plasma flame irradiation is difficult for pulse charging, and a laser beam can easily be concentrated its flux by a focusing lens to a beam diameter of several tens of 82 m, though the plasma flame irradiation is difficult to concentrate.

The gasified elements are cooled to solidify in an inert gas and are suspended in a form of fine particles. Since the gas outlet of the cell for generating the fine particles is connected to an excitation analyzer through the fine particle transfer pipe, the generated fine particles are carried by the inert gas in the generated state to the excitation analyzer. The cell for generating the fine particles is provided with a seal to close the gap between the cell and the specimen, and the carrier gas is stably introduced to the excitation unit.

In the excitation analyzer, a high temperature excitation flame excites the sample elements. The excitation flame is, for example, an acetylene combusted flame for an atomic absorption analysis, and an Ar plasma flame for a plasma emission analysis. The specimen can be introduced to such an excitation flame as a gas phase. Since the heated and excited elements in the passage in the excited flame absorb or emit specific spectra, it can be performed instantaneously to identify and measure, in quantity, the elements.

Also in the case of the plasma excition flame, elements are ionized and are introduced to a mass analyzer to carry out a mass analysis. The mass analysis requires not only investment cost but also lots of precautions of daily maintenance for maintaining the performance of the equipment. Accordingly, that type of equipment is not easily handled on a production line at least at present. The spectral analysis is rather applicable for practical use.

The methods described above improve the accuracy and correct value of analysis compared with the prior art. For some of the elements which are liable to segregate, further accuracy and correctness are required.

For the case of the fine particles, the uniformity and the quantity of the fine particles should be considered along with the selective vaporization. The state that the fine particles are being suspended in a carrier gas is analogous to a state that components are being dissolved in an aqueous sample solution. Therefore, if a large particle comes into an excited flame, it gives a high content of the composition concerned. A gas containing sufficiently dispersed fine particles should be introduced into the excited flame in a stable manner. When the quantity of components is at a level insufficient for analytical sensitivity, the correctness is degraded and noise ratio increases, and the accuracy is also degraded.

There are some differences among the methods for charging high density energy when they are strictly compared. Between the spark discharge and the pulse laser, the pulse laser gives superior charging condition. In the case of spark discharge, the discharge point occupies a very narrow area, and the control of the point is difficult since a selective discharge occurs at a place where it is easy to discharge. This phenomenon affects the specimen representativeness, though the degree of effect is not large. When the excitation analysis methods are comparatively studied, the plasma emission method is superior to the atomic absorption method in terms of analyzing non-metallic elements such as C, P, S, and of multi-element simultaneous analysis. In particular, an inductive coupled plasma (hereinafter referred to as "ICP") flame is broad and stable in its high temperature area, and the flame is suitable for exciting a substance in a fine particle state. In other words, it is an optimum combination that the pulsed laser beam is irradiated as the high density energy to generate fine particles and that the generated fine particles are transferred to ICP for analysis.

As for the laser beam irradiation, the selective vaporization and the rate of fine particle generation differ with the condition of irradiation. The relationship is summarized below.

By increasing the energy density at the irradiating spot, the selective vaporization is diminished, and the density of $10^8$ W/cm$^2$ or more suppresses the selective vaporization within an allowable limit. However, excess density induces what is called the "break-down phenomenon" which electrolytically dissociates the atmosphere such as Ar to generate plasma. Once the phenomenon appears, the laser energy stops contributing to the generation of the fine particles. For suppressing the selective vaporization without inducing the break-down phenomenon, it is optimum to select the energy density at the irradiating spot in a range of from $10^8$ W/cm$^2$ to $10^{11}$ W/cm$^2$. The fine particles generated under the condition were observed to find that the size was 0.1 μm or less, and the uniformity of distribution was satisfactory.

To increase the rate of fine particle generation and to secure the necessary quantity of fine particle sample, a specific laser output is naturally required. An oscillator giving the output of 5 W or more is sufficient for that purpose. Nevertheless, it is advantageous to charge energy within a short time, as described before, and the pulse laser is needed. Since a small frequency of pulse oscillation degrades the stable supply of the fine particles to the excition flame, an oscillation at 100 Hz or more is necessary. An oscillation at 100 Hz or higher level gives no difference of analytical accuracy independent of frequency. An oscillation of 20 Hz or less gives a significant difference from the analysis at 100 Hz or more.

Under a pulsed irradiation, the area where sample vaporized leaves a hole on the surface. In that case, the irradiating spot should rather be moved gradually to enlarge the hole for an easy vaporization and for an increased rate of fine particle generation than the repeated irradiation of laser beam to a fixed point to deepen the hole.

In addition, the moving irradiating spot increases the area for collecting a sample. This broadening the sampling area is important for analyzing elements which are easy to segregate. This mode avoids sampling exclusively the segregated concentrated zone or diluted zone, and improves the specimen respresentativeness. By irradiating the laser beam onto the surface of specimen while moving the irradiating spot at least 1 mm square, the sufficient rate of fine particle generation is obtained and the analytical accuracy (including for segregating elements) is improved.

The description given above concerns the conditions of irradiation in relation to the accuracy of analysis. In this respect, the collection of the fine particle sample is the collection of a part of the mother specimen as an aliquot thereof at a stable and necessary speed with no change of the comosition of the mother specimen, which sampling is an action for "grinding" from the viewpoint of the steel ingot. In other words, the condition for collecting the sample for analysis is an optimum condition for a grinding the steel ingot in view of mass. In grinding operation, however, it is not necessary to collect a sample at a stable speed, which is different from the collection of the sample for analysis. Nevertheless, similar to the collection of a sample for analysis, the grinding also requires avoiding any change of the mother specimen by selective vaporization and inclusion of a different phase. Furthermore, there is a layer to be removed, and a certain depth is necessary for the removal.

Figure 2:
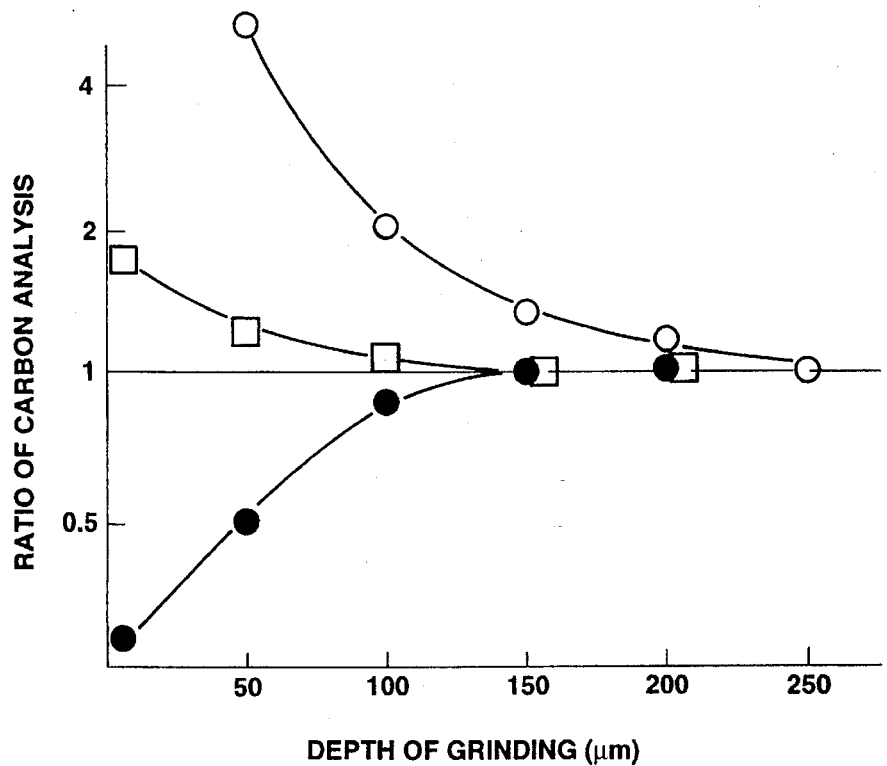
FIG. 2 is a graphic representation illustrating a relation between a grinding depth of a second grinding step and a ratio of analytical carbon content to an internal carbon content according to the Embodiment 1 of the present invention.

An example of the depth of a different phase gives several hundred μm. Carbon is one of the notified elements which are most likely to be affected by oxidation and which are the components of soil and which are difficult to obtain an accurate analytical result. FIG. 2 shows a relation of carbon content between a content in a depth direction and a content of a mother specimen. The horizontal axis represents the grinding depth, and the vertical axis represents a ratio of analyzed carbon content at each depth to the carbon content of the mother specimen. The figure gives the data on three types of steel ingots. The solid circle (●) designates the hot cast steel ingot treated by the first grinding step. The open circle (○) designates the peripheral surface of a rolled pipe, which was not treated by the first grinding step. The open square (□) designates an edge of a rolled pipe, which was not treated by the first grinding step. The hot cast steel ingot was given by the first grinding step, and the succeeding decarburization reduced the carbon content in the surface layer, but the second grinding step to a depth of approximately 100 μm exposed the face representative of the mother specimen. In the rolled pipe, a rolling lubrication oil should stain the surface, and the carbon content at the surface layer was high, the periphery region having the carbon content of 10 times or more. Nevertheless, when these surfaces were ground to a depth of 100 to 300 μm, a surface representing the mother specimen appeared.

In the case that the generation of a slight amount of a sample is carried out using the pulse laser irradiation, if the second grinding step is also conducted by the pulse laser irradiation, then there is no necessity for installing a grinding unit within the cell, which simplifies the equipment and which allows to very easily maintain cleanliness of the cell.

In the pulse laser grinding, the condition of irradiation is basically the same as the condition of the irradiation aiming to generate the fine particles. Accordingly, the range of energy density and the sweep irradiation area do not change. However, there are differences in the repeated sweep irradiation for at least around 10 times to secure the removing depth and in the irradiation at an increased oscillation frequency of 1 KHz or more.

For the movement of irradiating spot, it is easier even if the movement is made in high speed to operate a focusing lens or a reflection mirror than to move the specimen. The convergence is carried by a single-focus lens having a diameter of several millimeters over ten millimeters. The laser beam which has a parallel beam flux enters the center of the lens, and the transmitted beam converges on the focal point. When the lens is moved in parallel direction, the incident point also drifts from the center by the moved distance. However, the transmitted beam still converges on the focal point. Since the focal point moves in parallel along with the parallel movement of the lens, the converging point also moves by the distance of the movement of focal point. A reflection mirror is used to adjust the propagating direction of the laser beam sent from the oscillator and to guide to enter the center of the focusing lens. When the reflection mirror is rotated to displace the incident point on the lens, the incident angle to the lens changes, which results in a movement of the convergence point from the focal point.

The irradiating spot controller controls the reflection mirror by rotating the reflection mirror, or controls the parallel movement of the focusing lens to move the irradiating spot of the laser beam.

A high purity Ar gas is used as a carrier gas. Argon is an inert gas which is easily purified and which is widely used in practical application. The ICP flame is an Ar plasma. The use of Ar gas does not induce a new spectra including interfering line in the spectral analysis.

Carbon is one of the important elements which significantly affect the characteristics of steel. Carbon is needed for high accuracy and correct value for analysis, though it is a segregation element. Carbon exists in air at a large amount as carbon dioxide gas and hydrocarbons.

The purity of commercially available Ar is 99.995%. The analysis of carbon in the commercial Ar shows the carbon content ranging from 4 to 5 μg/liter. In an ICP flame, the gas is used at a volume of more than several liters over 10 liters as a plasma gas, and several more liters as an auxiliary gas and a carrier gas. The total amount of carbon as an impurity affects the accuracy of analysis of carbon in steel. When a getter was employed to purify the argon gas, the carbon content decreased to 0.2 μg/liter.

The carbon content in steel is several tenths of percent for ordinary steel. This content level corresponds to 1 μg/liter in the carrier gas. At the analysis, the carbon content contained in Ar gas is subtracted as a blank value to determine an analytical value. However, a high content of carbon in Ar gas gives a high fluctuation of the blank value.

Figure 3:
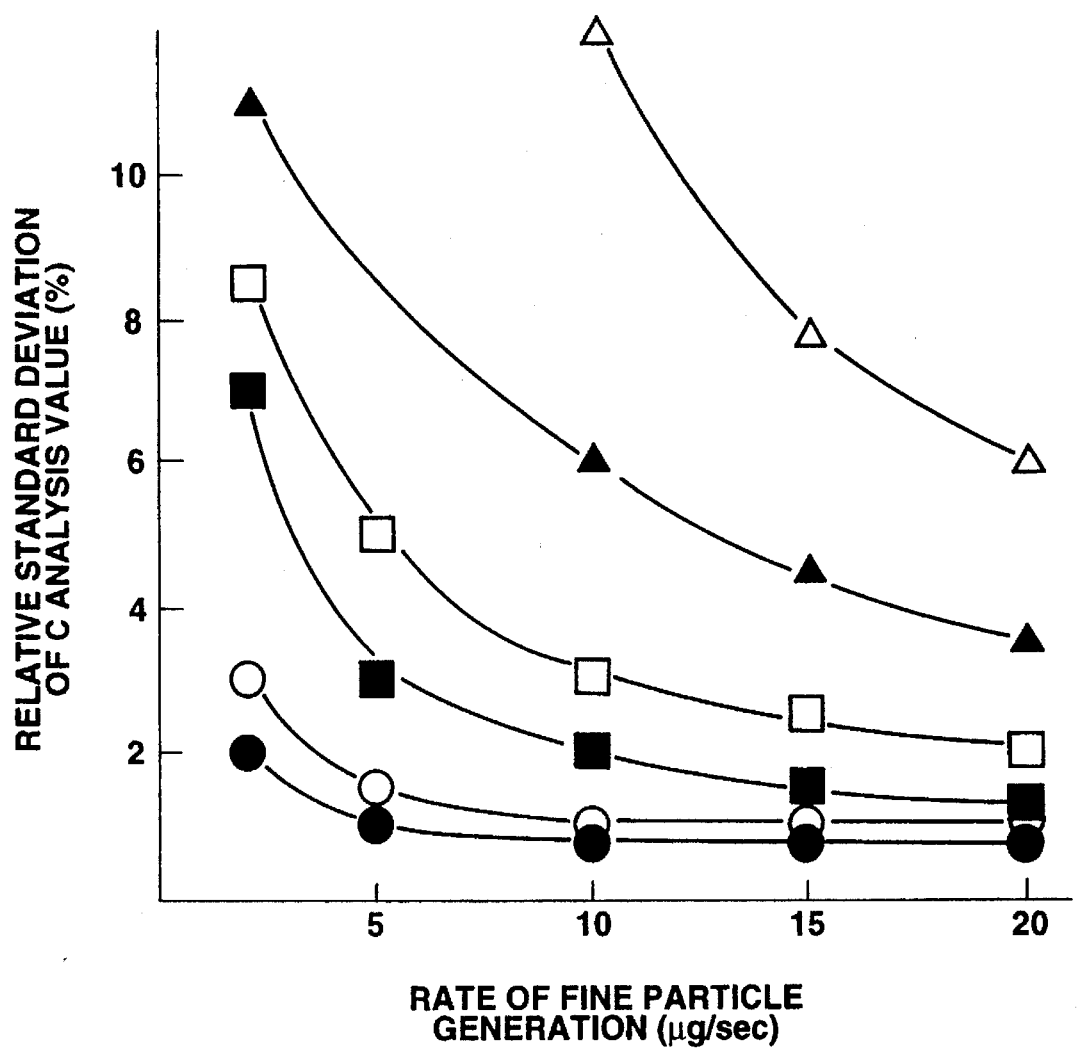
FIG. 3 is a graphic representation illustrating a relation between a rate of fine particle generation and a relative standard deviation of C analytical values according to the Embodiment 1 of the present invention.

FIG. 3 shows the effect of carbon content on the accuracy of carbon analysis. The graph shows the effect of the carbon content by changing the degree of purification of high purity Ar gas. The degree of effect differs with the quantity of a slight amount of sample and the carbon content in the specimen. The horizontal axis represents a rate of fine particle generation. The vertical axis represents a relative standard deviation. An open triangle (△) and a solid triangle (▲) show the carbon content of 5 μg/liter in Ar gas, an open square(□) and a solid square (■) show the carbon content of 1 μg/liter, and an open circle (○) and solid circle (●) show the content of 0.2 μg/liter. An open triangle(△), an square (□), and an open circle (○) show the case of carbon content in the specimen at 0.1%. A solid triangle (▲), a solid square(■), and a solid circle(●) show the case of carbon content in the specimen at 0.2%.

When an analytical accuracy of relative standard deviation aims at being within 2% for a specimen containing carbon at 0.1%, the carbon content in Ar gas is needed to be reduced to 1 μg/liter or less.

To achieve the target value, the inert gas generator is provided with an Ar purifier, and commercial high purity gas is further purified for the plasma flame and carrier use to reduce the carbon content to 1 μg/liter or less.

To protect the purified gas from contamination, the cleaning of a piping system and the selection of a piping material should be carefully done. In addition, general plastic materials and rubbers which have a possibility of gas permeation and which are difficult with respect of cleaning should be avoided. Metal or glass is preferable for the piping material.

Table 2 shows analytical results and true values of a cold steel ingot, where the analysis was carried out based on the above-described conditions. The true values are ones which were determined by a strict chemical analysis. As seen in the table, the analytical results showed quite a good agreement with the true values.

TABLE 2

| Component | Analytical Results | True Values |
| --- | --- | --- |
| C | 0.19 | 0.19 |
| Si | 0.19 | 0.19 |
| Mn | 0.69 | 0.68 |
| P | 0.012 | 0.011 |
| S | 0.002 | 0.002 |
| Cu | 0.004 | 0.004 |
| Ni | 0.02 | 0.02 |
| Cr | 0.03 | 0.03 |
| Mo | 0.006 | 0.006 |
| Al | 0.002 | 0.001 |

EXAMPLE

A fine particle sample was generated from a steel ingot using a pulse laser or a pulse DC (direct current) arc discharge as a high density energy. The generated sample was sent to an ICP for analysis. FIG. 1 shows an appraratus which uses the pulse laser.

In FIG. 1, the referential numeral 1 denotes a steel ingot. The referential numeral 2 denotes a grinding means for grinding surface of the steel ingot, which is mounted on a uni-directional stage 3. A grinding position is controlled by an automatic feed stage 5 which is provided with a cell mounting stage 4 and the grinding means 2. The reference numeral 6 denotes a cell for generating the fine particles. An end of the cell 6 has a cylindrical opening 7 which has sealing section 8 at a tip end of the cell. The other end of the cell 6 has a quartz window 9 through which the laser beam enters to irradiate onto the surface of the steel ingot 1 through the cell 6 for generating the fine particles. The reference numeral 10 denotes a gas inlet, and 11 denotes a gas outlet.

An oscillator 12, a reflection mirror 13, and a focusing lens 14 form a charge mechanism for charging a high density energy. The laser beam emitted from the oscillator 12 is adjusted its propagating direction by the reflection mirror 13, and is converged by the focusing lens 14. An angle of the reflection mirror 13 is controlled by an angle controller 15, and the position of the focusing lens 14 is controlled by a lens movement controller 16. With the control, the positioning and movement of an irradiating spot is conducted.

The referential numeral 17 denotes a carrier gas generator which sends a carrier gas to the gas inlet 10 through the gas transfer pipe 18. The gas outlet 11 connects an ICP emission spectral analyzer 19 through the gas transfer pipe 18 to analyze the generated fine particles.

A grinder is used for the grinding means 2 for generating the fine particles. The entire grinding means 2 is covered with a heat insulating plate (not shown) to shield radiant heat from the hot steel ingot except for the grinding means 2 and a feed section of the cell 6. The surface of the hot ingot at an analysis area was in an irregular state giving 2 to 3 mm of irregularity. The analysis area of about 30 mm×30 mm was treated by a belt grinder of #60 particle degree for about 10 sec. followed by a 150 mm diameter disk with zirconia abrasive grains for about 20 sec. The treatment gave a flat and smooth surface, and no heat effect was observed on the belt nor disk.

After the first grinding step, the grinding means 2 leaves from the steel ingot 1. The cell 6 for generating the fine particles which is mounted on the cell stage 4 then comes to the polishing surface following the control of the automatic feed stage 5. The cell stage 4 moves to let the cell 6 cover the polishing surface.

The cell 6 is made of copper, and the end facing of the steel ingot has a cylindrical opening having dimensions of 20 mm in inner diameter, 26 mm in outer diameter, and 5 mm in length. The tip end of the cylindrical opening has a groove to form the sealing section 8 which has an inserted sealing material of ceramic fiber blended with a low melting point glass powder. The glass powder becomes a viscous melt on receiving the heat of steel ingot, which enhances the sealing action by filling a gap between the steel ingot and the cell 6.

The second grinding step was carried out using laser beam irradiation. The used oscillator 12 was Nd-YAG laser (wave length 1.06 μm) with an ultrasonic wave Q-switch. The oscillator was common to the generation of fine particles. The condition of irradiation for the grinding was oscillation frequency of 10 KHz, energy density at the irradiating spot of $10^9$ W/cm$^2$, and repeated scanning irradiation for 10 times over a 2 mm square area. The scanning was conducted under a high speed movement being enabled by the change of reflection angle of the reflection mirror 15 and by the parallel movement of the focusing lens 14 in lateral direction to the high speed movement.

In the case of spark discharge, the charging mechanism of high density energy differs from the case of laser beam. Accordingly, the cell structure was selected to provide an electrode in the cell 6 for generating the fine particles to use an edge face as a counter electrode. The second grinding step used also a discharge method, which is the same as in the case of laser beam, repeating a cycle of 5 second discharge and 3 second intermission for 5 times in total. The conditions for discharge were 400 V, C=10 μF, L=10 μH, R=2Ω, and frequency of 400 Hz.

Argon was used as the carrier gas. The carrier gas generator 17 comprised an Ar cylinder and a Zr getter gas purifier. The gas transfer pipe was made of stainless steel which was cleaned in advance.

As for the ICP emission spectral analysis, a direct excitation emission of the coming fine particles was used under the conditions of frequency of 27.12 MHz, output of 1.5 KW, plasma gas flow rate of 15 liter/min., auxiliary gas flow rate of 1 liter/min., sample gas (carrier gas) flow rate of 1 liter/min. The spectrometer was a Paschen-Runge spectrometer, which was evacuated in the device to enable to the measurement of 200 nm or shorter. The applied analytical lines were 193 nm for C, 178 nm for P, 181 nm for S, 212 nm for Si, 252 nm for Mn, 396 nm for Al, 232 nm for Ni, 268 nm for Cr, 202 nm for Mo, 325 nm for Cu, 229 nm for Co, 311 nm for V, 335 nm for Ti, 309 nm for Nb, 183 nm for B, 318 nm for Ca, 355 nm for Ar, 271 nm and 170 nm for Fe. A slit and a photoelectric multiplier were placed at every analytical line position to structure a multi-elements determination system.

The beam intensity was converted to current and further to voltage through the photoelectric multiplier, and a cumulative value of beam intensity over 10 sec. range was adopted as a measured beam intensity. The analysis used an intensity ratio method which adopts a ratio to an iron intensity as a measured value. The conversion of the measured value to the analytical value was conducted by using an analytical curve prepared from the determination of a standard specimen containing known composition. Table 3 shows the composition of the specimen used.

TABLE 3

| Componenent | Content (%) |
| --- | --- |
| C | 0.22 |
| Si | 0.21 |
| Mn | 1.38 |
| P | 0.02 |
| S | 0.010 |
| Cr | 0.32 |
| Mo | 0.12 |
| Cu | 0.01 |
| Ni | 0.02 |
| Al | 0.035 |

For comparison, studies were carried out on comparative examples which were outside of the scope of the present invention and on prior art examples in which the fine particles were generated by plasma irradiation. Table 4 shows the accuracy and correctness of the analytical values expressed by relative standard deviation for each condition of fine particle generation and of major components.

According to the Examples of the present invention, the relative standard deviation is in a satisfactory range, within 5%, even when the hot steel ingot is analyzed. In particular, the test Nos. 4, 5, and 6 which were carried out under a favorable condition using the pulsed laser showed the relative standard deviation of within 2%, which values suggest extremely high accuracy and correctness of the analysis.

On the other hand, the prior art Examples unavoidably accompanied inclusion of a different phase, and the carbon analysis was impossible. In addition, other components gave a large deviation.

Also in the Comparative Examples, the test No. 8 in which high purity Ar gas was used without further purification could not perform the carbon analysis. The test No. 7 gave insufficient energy density and large relative standard deviation, which resulted in a poor accuracy and correctness.

Embodiment-2

When a lump sample in a red heat state is handled at a room temperature, a temperature of the sample changes with time. If a pulse laser beam is irradiated onto the sample, which changes its temperature, to generate fine particles, the effect on the analytical result becomes seriously important.

Since the irradiation of the pulse laser beam impresses a high density energy, the irradiating spot attains a very high temperature. During the process of the fine particle generation, the requirement is to convert a portion of the sample accurately into fine particles, and there is no need to control the state of excitation of element as required in the emission analysis. Accordingly, the effect of the temperature of the sample should be very small. To confirm the speculation, a laser/ICP analysis was carried out using a sample taken from a steel ingot which was heated to 1000° C. or more and applying the pulsed laser beam to the lump sample which is in the process of being cooled.

Figure 6A:
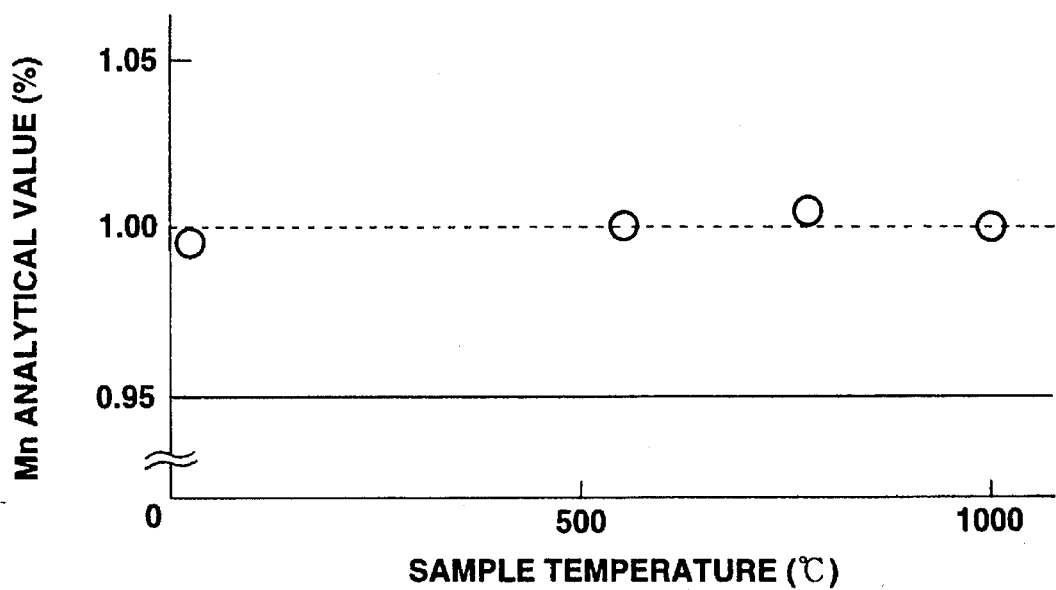
FIG. 6(A) and FIG. 6(B) are graphs which show a relation between a temperature of a sample and an analytical value according to the Embodiment-2 of the present invention.
Figure 6B:
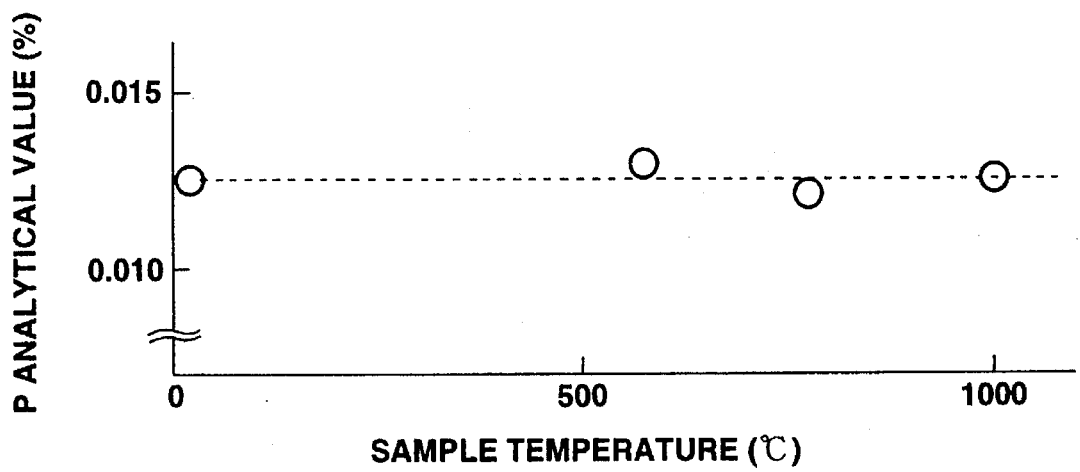

The results are shown in FIG. 6(A) and (B). The vertical axis represents analyzed values, and the horizontal axis represents temperatures of a samples. FIG. 6(A) shows the result for Mn analysis. FIG. 6(B) shows the results for P analysis. For both components, there appeared very slight changes in analytical values with the temperatures, and there can be no affects by the temperatures.

Even for a lump sample which shows changes of temperatures at a red heat state, the laser/ICP analysis which generates the fine particles by irradiating a pulse laser beam does not substantially effect the temperature of the sample with respect to the analytical values, and reliable analytical results are assured. For the sample which is cooled, the

TABLE 4

| Items | Test No. | Condition of Fine Particle Generation | | | | | Relative Standard Deviation (%) Elemental Analysis | | | | | | |
| --- | --- | --- | --- | --- | --- | --- | --- | --- | --- | --- | --- | --- | --- |
| | | Mode of Energy | Energy Density (W/Cm$^2$) | Frequency (Hz) | Area of Irradiating Spot Movement (mm$^2$) | Ar gas Purification | C | Si | Mn | P | S | Cr | Mo |
| Example of Present Invention | 1 | Spark | $5 \times 10^8$ | 60 | — | Yes | 4.8 | 3.8 | 2.8 | 4.2 | 4.5 | 1.5 | 1.7 |
| | 2 | Laser | $1 \times 10^{11}$ | 500 | 0.5 | Yes | 4.1 | 1.8 | 1.5 | 2.2 | 2.9 | 0.6 | 0.8 |
| | 3 | Laser | $1 \times 10^{10}$ | 50 | 2 | Yes | 3.8 | 1.5 | 1.4 | 2.3 | 2.7 | 0.8 | 1.0 |
| | 4 | Laser | $1 \times 10^8$ | 100 | 4 | Yes | 1.0 | 0.9 | 0.5 | 1.7 | 1.8 | 0.6 | 0.7 |
| | 5 | Laser | $5 \times 10^9$ | 1000 | 1 | Yes | 1.2 | 1.0 | 0.4 | 1.9 | 1.8 | 0.5 | 0.6 |
| | 6 | Laser | $5 \times 10^8$ | 5000 | 2 | Yes | 1.1 | 0.8 | 0.5 | 1.8 | 1.9 | 0.6 | 0.6 |
| Comparative Example | 7 | Laser | $1 \times 10^7$ | 500 | 2 | Yes | 14.5 | 3.7 | 2.6 | 8.2 | 11.8 | 1.5 | 7.7 |
| | 8 | Laser | $1 \times 10^9$ | 100 | 2 | No | Unacceptable | 1.2 | 0.7 | 2.1 | 2.3 | 0.9 | 1.1 |
| Conventional Example | 9 | Plasma | $5 \times 10^4$ | — | — | Yes | Unacceptable | 7.9 | 9.7 | 14.8 | 17.6 | 4.7 | 8.5 |
| | 10 | Plasma | $1 \times 10^4$ | — | — | Yes | Unacceptable | 19.6 | 22.3 | 48.5 | 51.6 | 5.4 | 29.9 | temperature change becomes less. Therefore, needless to say it is natural that the reliability in the analysis is also ensured.

Figure 7A:
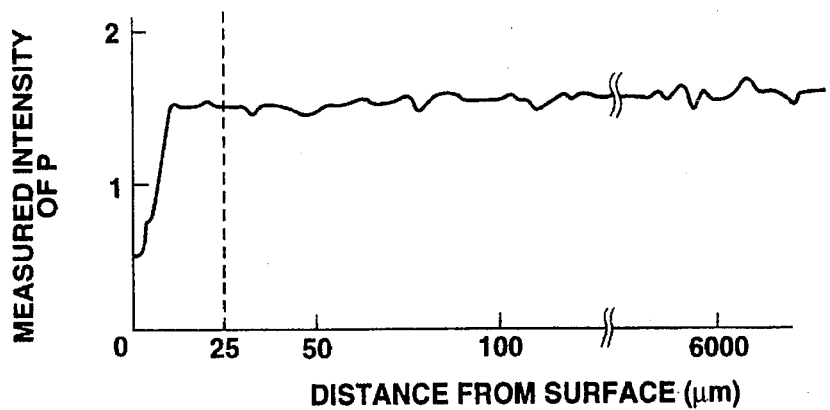
FIG. 7(A), FIG. 7(B) and FIG. 7(C) are graphs which show, respectively, a relation between a distance from a surface of a specimen and a measured intensity according to the Embodiment-2 of the present invention.
Figure 7B:
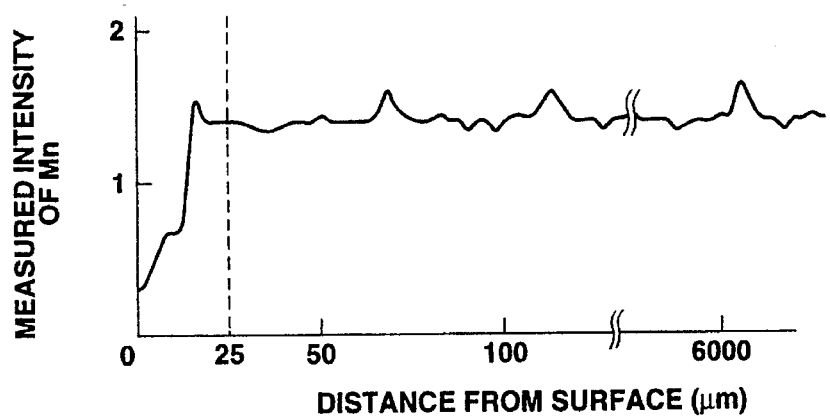
Figure 7C:
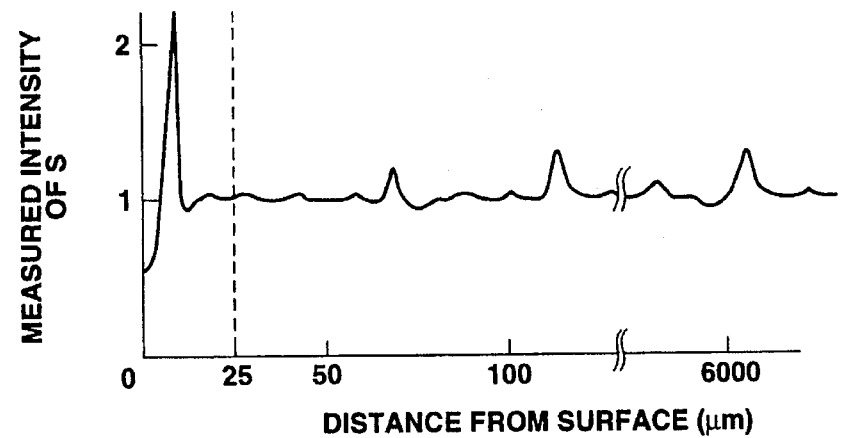

For a sample which was prepared by solidifying molten steel, a surface layer of the sample was affected by oxygen in air to some degree, and the surface layer does not represent the composition of the sample. The results of the study of the effect are shown in FIG. 7(A) and FIG. 7(B). These are the results obtained from a method where the analysis from a side face toward an inside of the sample was given by using SIMS(secondary ion mass spectgraphy) and XMA(X-ray micro analyzer) to a sectional plane of the sample which was prepared to be a truncated cone shape having minor diameter of 30 mm and major diameter of 33 mm. The analyzed components are P, Mn, and S. The vertical axis shows the measured intensity for each component, and the horizontal axis shows the distance from the surface.

For all components determined, the measured values change upto several μm over ten μm. At a depth of 25 μm or more, however, the measured values become the same level with that of the inside of the sample, where there occurred no effects of oxygen in air. The small peaks observed on Mn and S coincide each other, which suggests that segregated MnS inclusion exsists.

Since laser beam irradiation easily removes tile surface layer for an approximate depth of 25 μm, a portion of the fine particles generated in initial stage of irradiation is discarded, and only the fine particles generated from a depth of 25 μm or deeper are collected for the analysis. This procedure allows to collect the fine particles representing the sample adequately without the pre-treatment of cutting or polishing the sample.

Nextly, contamination and selective vaporization are also the problems of degradation of the representativeness of the fine particle sample. As for the degradation of accuracy of ICP analysis, the rate of fine particle generation and the fluctuation of size and the transferring amount of fine particles become problems.

Since the ICP analysis excites the transferring fine particles with Ar plasma, it is preferable to use a high purity Ar gas as the carrier gas because the gas does not contain inhibitor elements. Commercially available high purity Ar gas, however, contains carbon at a level of several μg/liter in a form of hydrocarbons. If the impurity carbon is decreased to 1 μg/liter or less, the Ar gas allows an accurate analysis of a slight amount of carbon in steel.

A metallic getter purification unit can be applied to remove the impurity carbon. The purification unit can be installed in the piping system for sending a carrier gas to a sample chamber. For preventing re-contamination of the carrier gas in the supply piping, the piping is constructed by a metal or glass which easily give a clean wall surface.

The degree of selective vaporization, the rate of fine particle generation and the size of generated fine particles are affected by the condition of irradiation of the laser beam.

The reason why the pulse laser is applied is to increase the laser beam irradiating spot density and to decrease the selectivity of vaporization. If the laser beam irradiating spot density is small, the rate of fine particle generation is low, which induces insufficient ICP sensitivity and increases selectivity of vaporization. If the laser beam irradiating spot density is excessively large, the Ar gas electrolytically dissociated to generate plasma, which is called the "breakdown phenomenon". If the phenomenon appears, the energy of the laser beam does not contribute to the generation of the fine particles. An allowable range of the laser beam irradiating spot density is in a range of from $10^8$ W/cm$^2$ to $10^{11}$ W/cm$^2$. Within this range, the obtained fine particle size is 0.1 μm or smaller, and the size is accepted as uniform particle size distribution in an ICP flame.

The analytical accuracy in the case of pulse frequency of 20 Hz gives a significant difference from the accuracy at 100 Hz or more, and gives a poor accuracy. This is presumably due to a low frequency being unable to stabilize the supply of fine particles to ICP flame. The frequency of 100 Hz or more induces no difference in analytical accuracy and gives a good result.

A consecutive irradiation of high frequency pulse on a same spot enhances selective vaporization, and generates a drift between the irradiating face and the focal point along with the repeated irradiations to decrease the amount of the generated fine particles. These two problems are solved by moving the irradiating spot, and the moving irradiating spot also avoids a severe effect of segregated section on the analytical result.

Now, the invention will be described with reference to FIG. 4. The referential numeral 101 denotes a analytical cell section; 102 a sample holding section; 103 a lump sample; 104 a laser oscillator; 107 a carrier gas piping, 108 an ICP analyzer; 110 a laser beam; and 121 an exposure hole.

A sample chamber comprises the analytical cell section 101, and the sample holding section 102 is connected to the analytical cell section 101 through the exposure hole 121. The sample 3 is charged into the sample holding section 102. The laser beam 110 is emitted from the laser oscillator 104, passes through the analytical cell section 101 and exposure hole 121, and irradiates onto the surface of the sample 103. To prevent oxidation, the analytical cell section 101 and the sample holding section 102 are under an inert atmosphere. The inert carrier gas is introduced into the analytical cell section 101. The fine particles generated by the laser beam irradiation are introduced to the ICP analyzer 108 through the carrier gas piping 107 along with the carrier gas, and the analysis is conducted at the ICP analyzer 108.

For assuring a high analytical accuracy, it is important to supply the generated fine particles to the ICP analyzer 108 at a constant rate. The steady supply of these fine particles to the ICP analyzer 108 can be assured when the sample hold means 102 has the same curved face with that of the sample 103 because both of these curved faces contact each other closely to the exposure hole 121 by the side face of the sample 103 to prevent the carrier gas containing fine particles from escaping to the sample holding section 102.

In addition, when the lump sample is positioned while contacting the side face of the sample 103 to the exposure hole 121, the focal point of the laser beam 110 can be fixed, which shortens the control time.

Regarding the insertion and withdrawal of the sample 103, since the sample chamber is divided into the analytical cell section 101 and the sample holding section 102, there is no need for exposing the cell analytical section 101 to air during the insertion and withdrawal of the sample. As a result, a step for sweeping the air in the cell analytical section 101 with an inert gas is eliminated.

Since the sample holding section 102 is exposed to air during the step of the insertion of the sample, the sweeping with inert gas is necessary after the insertion of the sample. If, however, the sample holding section 102 has the same curved face with that of the sample 103, the gap between the sample holding section 102 and the sample 103 becomes narrow, and the necessary amount of the sweep gas becomes small, and the time for sweeping is also reduced.

The change of composition of the sample is a problem peculiar to the sample being red-heated. The decarburization owing to oxygen in air at the surface layer affects the carbon analysis value.

This is why to impart a mechanism of anti-oxidation the sample at the sample holding section. It is wanted not only to accommodate the lump sample in the sample hold means under an inert atmosphere but also to cool the sample as fast as possible.

EXAMPLE

Figure 4:
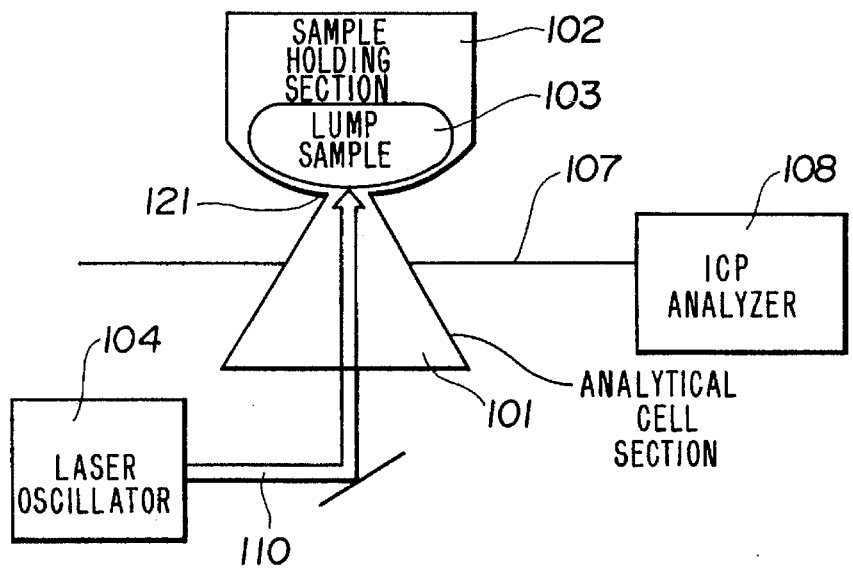
FIG. 4 is a schematic view illustrating an apparatus for analyzing steel according to an Embodiment-2 of the present invention.
Figure 5:
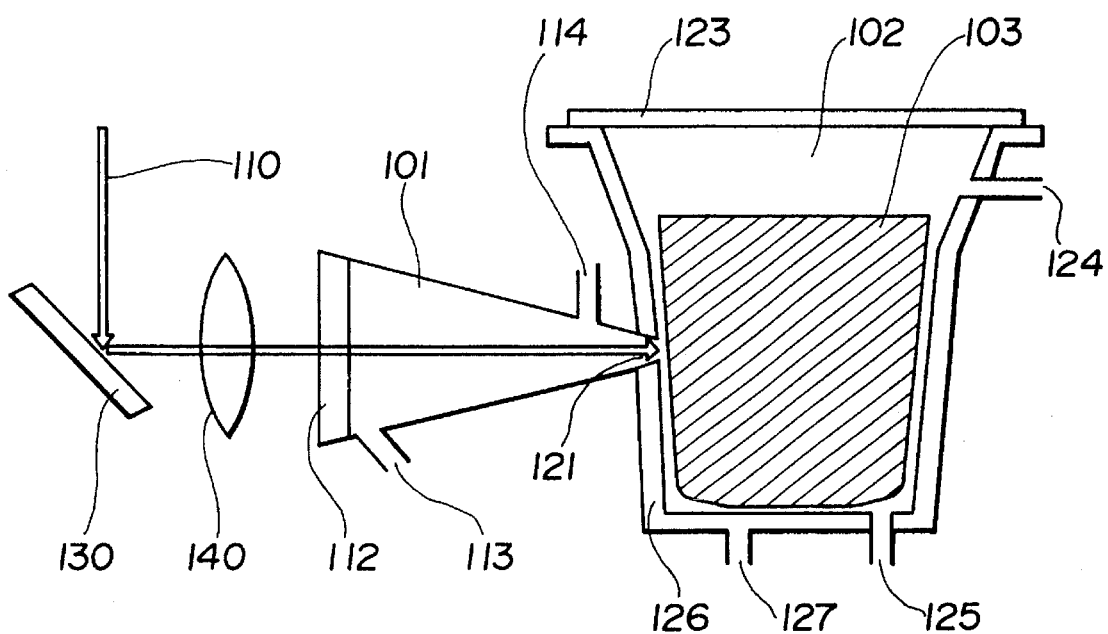
FIG. 5 is a schematic view illustrating another apparatus for analyzing steel according the Embodiment-2 of the present invention.

A lump sample which was taken from a converter and was cooled to be solidified was analyzed using the sample chamber shown in FIG. 4. The sample had a shape of truncated cone with a bottom diameter of 30 mm, a top diameter of 33 mm, and a height of 70 mm.

The inside dimensions of the sample holding section 102 were a bottom diameter of 30.5 mm and a height of 120 mm, having a vacant space which has the same curved face with that of the sample 103. At the top portion of the sample holding section 102, there was a gas inlet nozzle 124. At the bottom portion of the sample holding section 102, an exhaust nozzle 125 was provided to connect to a suction pump (not shown). The replacement of atmosphere to the inert gas after the insertion of the lump sample was carried out in a short time to prevent the oxidation of the sample.

Surrounding walls were the double-wall made of copper. Cooling water was introduced into a space 126 between the walls to protect the walls and to cool rapidly the sample 103 to prevent oxidation of the sample as far as possible. Accordingly, the quick gas replacement and the high speed cooling mechanism played a role of anti-oxidation mechanism. The exposure hole 121 had a rectangular opening of 4×8 mm.

To the assure a sufficient contact between the side face of the sample 103 with the exposure hole 121, the sample chamber was set to maintain the sample holding section 102 at a 45 degree inclination to the vertical direction.

The analytical cell section 101 also had a shape of a truncated cone, and the side facing the exposure hole 121 was a laser transmission window 12 made of quartz glass. A carrier gas inlet 113 was provided at near a transmission window 112, and a gas outlet 114 was provided at near the exposure hole 121. An Ar gas was used as the carrier gas, and a Zr getter purifier was employed for purifying the Ar gas. The piping was constructed using SUS pipe of which the surface was cleaned.

The laser oscillator used Nd/YAG laser (wave length of 1.06 μm) with an ultrasonic wave Q switch, and the irradiating spot and focal point were controlled by the reflection mirror 130 and the focusing lens 140. The movement of the irradiating spot could be performed by rotation of reflection mirror or by parallel movement of focusing lens. In other words, the focal point is defined by the focusing lens, and the irradiating spot is moved in a mono-axial direction by the rotation of the reflection mirror 130. On the other hand, if the focusing lens 140 is moved in a parallel direction within a range of effective diameter, the irradiating spot moves in the same direction by the same distance of the movement of the focusing lens 140. By combining these two movements, the irradiating spot was moved in a two-dimensional mode to conduct the scanning irradiation.

The analysis was performed in the following procedure.

A commercially available Ar gas was used as the inert gas, and the purification of the Ar gas reduced the C content of 4–5 g/liter to 0.2 μg/liter.

The surface temperature of the sample 103 immediately before analyzing was 1100° C. The sample was placed in the sample holding section which received the Ar gas flow at a rate of 10 liter/min. The sample holding section was evacuated by a suction pump to 1 atmosphere, then both the gas inlet and the gas outlet were closed. The time required for the operation was about 5 sec. During the period, the cooling water was kept flowing.

The reflection mirror was rotated at a frequency of 30 Hz until the drift width of the convergent point became 2 mm long. The focal lens was moved in a parallel mode at a speed of 5 mm/min. to move the irradiating spot. The moving speed was 300 mm/min., and the spot diameter of focal point the was 100 m. The movement is preferably done over 1 mm square or more, and the moving speed is preferably carried out using an index of the product of a beam diameter and a pulse frequency.

As a preliminary treatment, 10 sec. of scanning irradiation was given to remove a surface layer by the depth of 200 μm. Then, the measurement was conducted.

The flow rate of carrier gas was 1 liter/min. The laser light irradiation was carried out at a pulse frequency of 50 Hz or 1 kHZ, and average output of 10 W.

An ICP emission spectral analyzer was used as the ICP analyzer. Regarding the conditions of plasma generation, the high frequency output was 1.5 KW, the frequency was 27.12 MHz, the plasma gas flow rate was 15 liter/min., and the auxiliary gas flow rate was 1 liter/min. The transferred fine particles were directly emitted.

A Paschen-Runge spectrometer was used as a spectrometer. The spectrometer was evacuated to allow the measurement of wave length of 200 nm or more. The applied analytical lines were 193 nm for C, 178 nm for P, 181 nm for S, 212 nm for Si, 252 nm for Mn, 396 nm for Al, 232 nm for Ni, 268 nm for Cr, 202 nm for Mo, 325 nm for Cu, 271 nm and 170 nm for Fe. A multi-elements determination system was used.

The beam intensity was converted to current and further to voltage through the photoelectric multiplier, and the cumulative value of beam intensity over 10 sec. range was adopted as the measured beam intensity. The analysis used an internal standard intensity ratio method which adopts the ratio to the iron intensity as the measured value. The conversion of measured value to the analytical value was conducted by using an analytical curve prepared from the determination of a standard specimen containing known composition.

Table 5 shows the result of the analysis and the time for the analysis including the preliminary treatment comparing with the spark emission method which was used in prior art.

Example 1 was conducted under a laser light irradiation at a pulse frequency of 50 Hz, and Example 2 was conducted at 1 kHz. In both cases, the measurement was carried out from the solidified samples taken out from the same molten steel.

TABLE 5

| Items | Sample | Analytical Value | | | | | Evaluation on Analyzed Value | Time of Analysis (sec) |
|---|---|---|---|---|---|---|---|---|
| | | C | Si | Mn | P | S | | |
| Example 1 | 1 | 0.09 | 0.01 | 0.13 | 0.022 | 0.005 | Excellent | 58 |
| | 2 | 0.12 | 0.02 | 0.12 | 0.024 | 0.006 | Fair | 60 |
| | 3 | 0.14 | 0.01 | 0.14 | 0.017 | 0.004 | Fair | 61 |
| | 4 | 0.13 | 0.02 | 0.10 | 0.020 | 0.005 | Fair | 60 |
| Example 2 | 5 | 0.10 | 0.01 | 0.12 | 0.022 | 0.005 | Excellent | 59 |
| | 6 | 0.11 | 0.01 | 0.11 | 0.021 | 0.005 | Excellent | 60 |
| | 7 | 0.10 | 0.01 | 0.11 | 0.020 | 0.005 | Excellent | 61 |
| | 8 | 0.10 | 0.01 | 0.11 | 0.021 | 0.005 | Excellent | 60 |
| Prior Art Example | 9 | 0.36 | 0.04 | 0.15 | 0.017 | 0.006 | Bad | 127 |
| | 10 | 0.07 | 0.01 | 0.11 | 0.017 | 0.004 | Fair | 128 |
| | 11 | 0.10 | 0.00 | 0.12 | 0.022 | 0.005 | Excellent | 124 |
| | 12 | 0.00 | 0.30 | 0.37 | 0.099 | 0.029 | Bad | 125 |
| | 13 | 0.01 | 0.01 | 0.12 | 0.022 | 0.004 | Excellent | 125 |

According to the Examples of the present invention, the difference of analyzed values among the samples is small. However, in the prior art Examples, the difference is significant as seen in C analytical value, giving a range of from 0.00 to 0.36%.

In a spark emission, the range of discharge per one analysis cycle is approximately 6 mm in diameter. If, however, an irregularity caused by, for example, pin holes exists, the convex area is likely to induce discharge, and an abnormal discharge unavoidably occurs. The phenomenon presumably gives a considerable difference of analytical values among the samples.

In a laser irradiation, however, even when an irradiating range has protrusions, there is no possibility to concentrate the irradiation onto the protruded sites. The problem of laser irradiation rather lies on a selective vaporization and a stable generation of fine particles at a certain amount. Particularly in Example 2 where the condition of laser irradiation was limited, even a segregation component gave very high reproducible accuracy.

Furthermore, when the analytical period was compared, Example of this invention which did not need cooling of solidified sample completed the analysis in about 60 sec. after solidifying the molten steel, which shortened the analytical period to shorter than half of the prior art process.

According to the present invention, the laser irradiation generates fine particles from a lump sample, and excites the generated fine particles. Accordingly, no abnormal discharge is induced, which is observed in the prior art spark emission method, and the analytical result is free from the effect of sample temperature. As a result, there is no need of cooling, cutting, and polishing the solidified sample. With a special design for setting a sample to the analyzer, the rapid analysis of molten steel composition is performed. Furthermore, change of sample state, contamination of fine particle sample, rate of fine particle generation, stability of fine particle generation, and selective vaporization are also considered to give a high accuracy to analytical values.

With these measures, the data feedback to the steel making operation control became prompt, and the control accuracy on molten steel composition and temperature was improved. As a result, the rate of defectives on the composition was reduced, the efficiency reduction caused by post-blowing and by adding coolant was prevented, and energy saving was obtained. In this respect, the effect of the present invention for enabling the analysis of a red heat sample has a significant meaning.

EMBODIMENT-3

A focused laser beam irradiation extremely increases an energy density at a focal point, so the sample near the focal point is gasified and emitted. The emitted sample is solidified to form fine particles and is collected. The phenomenon is observed not only in steel but also in high boiling point materials such as ceramics. As a result, there is no need of cutting a sample for analysis off from a mother steel material nor preliminary treatment.

In addition, the fine particles generated by irradiating a laser beam onto a analytical surface are collected for 10 to 30 sec., and the collected fine particles are analyzed by a detector at the same time. The method offers a rapid analysis.

Causes of abnormality do not necessarily exist only at a surface layer, and sometimes the causes exist in a deep area, 50 μm from the surface, for example, which is often observed for the case of inclusions in a surface coated steel sheet.

Figure 10:
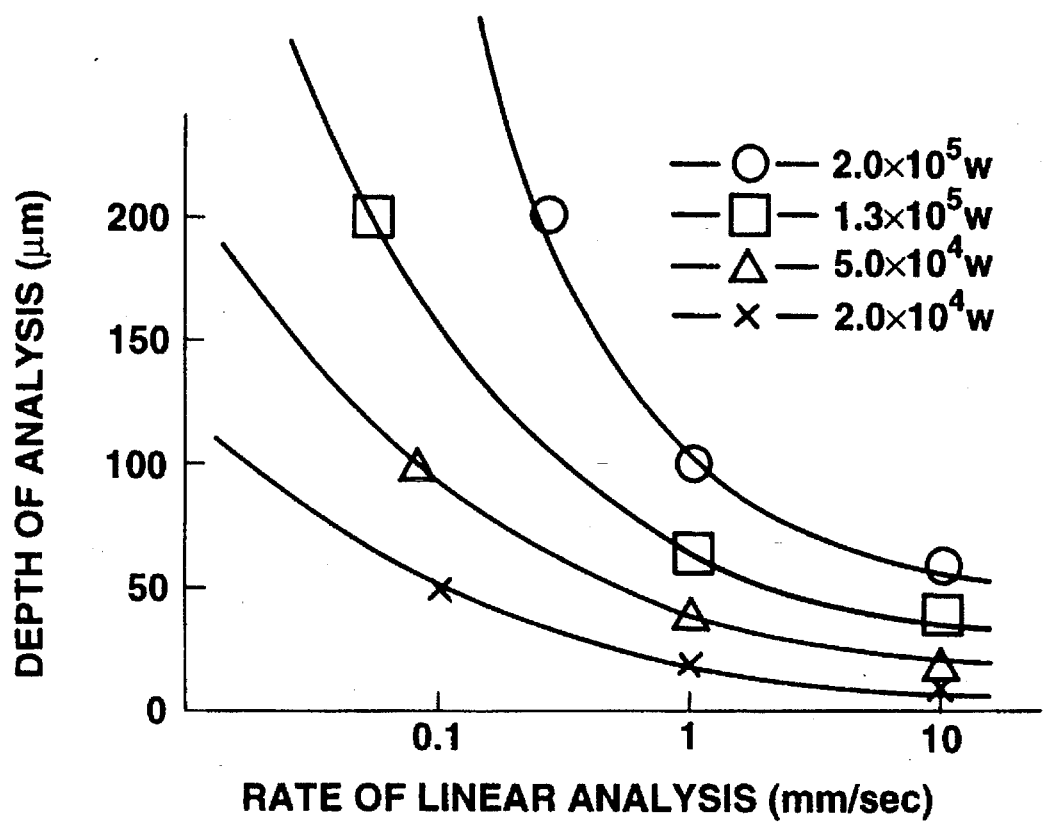
FIG. 10 is a graphic representation showing a relation among a peak output of a pulsed lazer beam, a speed of an irradiating spot movement and a depth of analysis according to the Embodiment-3 of the present invention.

FIG. 10 shows a case that the irradiation of pulse laser at an oscillation frequency of 100 Hz while moving the irradiating spot of laser beam, showing a collection depth of fine particles, namely an analytical depth. The pulse peak output varied from 20 to 200 kW. The higher the peak output is, the deeper the analytical depth is, and naturally, the lower the linear analytical speed is, the deeper the analytical depth is. It is easy to adjust the analytical depth in a range of from about 1 μm to 200 μm. For a further increase of the linear analytical speed while maintaining the analytical depth, a larger oscillation frequency is preferable.

Although the emission of elements at a depth of 20 μm in a steel material is difficult under an excitation by discharge, the pulse laser irradiation allows the detection of components for a wide range because the pulse irradiation can adjust the analytical depth. Accordingly, the pulse irradiation does not overlook the component which causes the abnormality under the study.

The laser irradiating spot is moved not only for adjusting the analytical depth but also for scanning the abnormal zone and its periphery. The movement of the laser irradiating spot is conducted by the rotation of a reflection mirror and by the parallel movement of a lens. The laser beam which is adjusted its propagating direction by the reflection mirror enters at the center of the focusing lens in a vertical direction to converge the beam on the irradiating spot of a steel material surface. When the reflection mirror is tilted, the incidence angle to the focusing lens changes, and the position of the focal point moves. If the focusing lens is moved in parallel while the reflection mirror is kept un-moved, the laser beam entering vertically to the lens converges at the focal point of the focusing lens. Since the focal point lies on the straight line passing through the focusing lens and vertical to the lens, the focusing point or the irradiating spot moves by the distance same as that of the lens.

By utilizing this principle, when the irradiating spot is moved by the rotation of the reflection mirror, by the parallel movement of the laser beam focusing lens, or by the combination of both movements, the irradiating spot can be rapidly moved in a two-dimensional direction, even if the fine particle collection cell or the large steel body are not moved. Particularly when both the depth direction and the line width of linear analysis are needed to secure for determining the components which cause abnormality, the irradiating spot can be moved in a zig-zag mode by combining the rotation of reflection mirror and the parallel movement of focusing lens. The method allows to conduct not only the linear analysis but also the two-dimensional scanning.

In the case that the steel sample or the fine particle collection unit moves, either one of the rotation of reflection mirror or the parallel movement of focusing lens enables to perform zig-zag movement of the irradiating spot.

Figure 9:
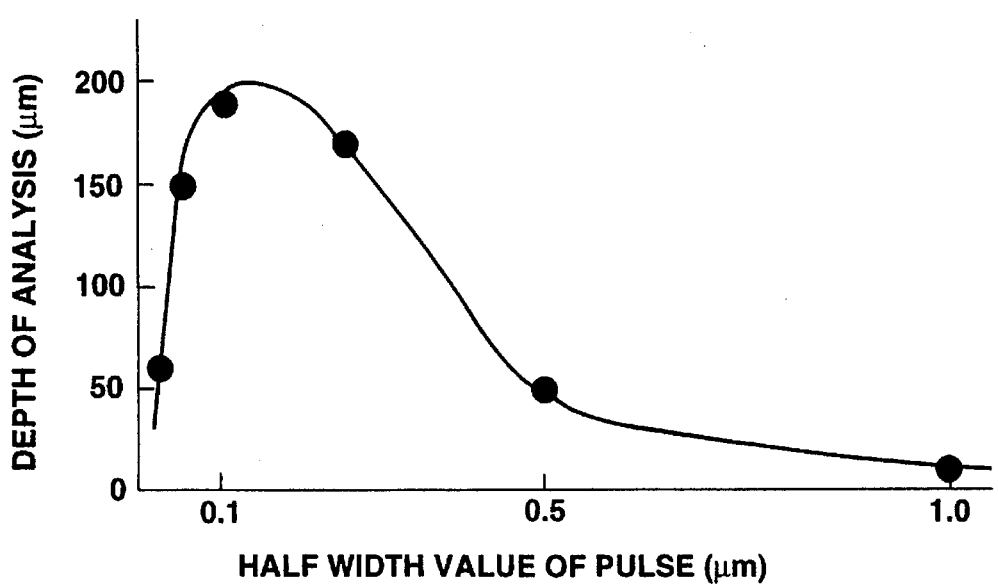
FIG. 9 is a graphic representation showing a relation between a half width of a pulsed laser beam and a depth of analysis according to the Embodiment-3 of the present invention.

The half width of pulse is another factor which affects the analytical depth. FIG. 9 shows an analytical result under a varied half width of pulse with a fixed values of irradiating spot moving speed being 0.5 m/sec., and of peak output being 200 kW. If the analytical depth is wanted to deepen, the half width of pulse can be selected in a specified range.

In the case that the depth where a component causing the abnormality exists cannot be estimated in advance, the selection of an analytical depth to 50 μm or more prevents overlook. In this case, the half width of pulse is selected in a range from 0.02 to 0.5 μsec., and the analysis at a desired depth is carried out by varying the peak output or the moving speed of irradiating spot. However, if the peak output is less than 20 kW, then the moving speed of the irradiating spot needs to be lowered. Accordingly, for a practical purpose, the peak output is preferably at 20 kW or higher. Excess peak output induces a phenomenon that the whole atmosphere generates plasma. Once the phenomenon appears, the plasma-formation consumes energy, and the amount of generated fine particles decreases. Therefore, the peak output is needed to suppress at 5 kW or lower level.

EXAMPLE

Figure 8:
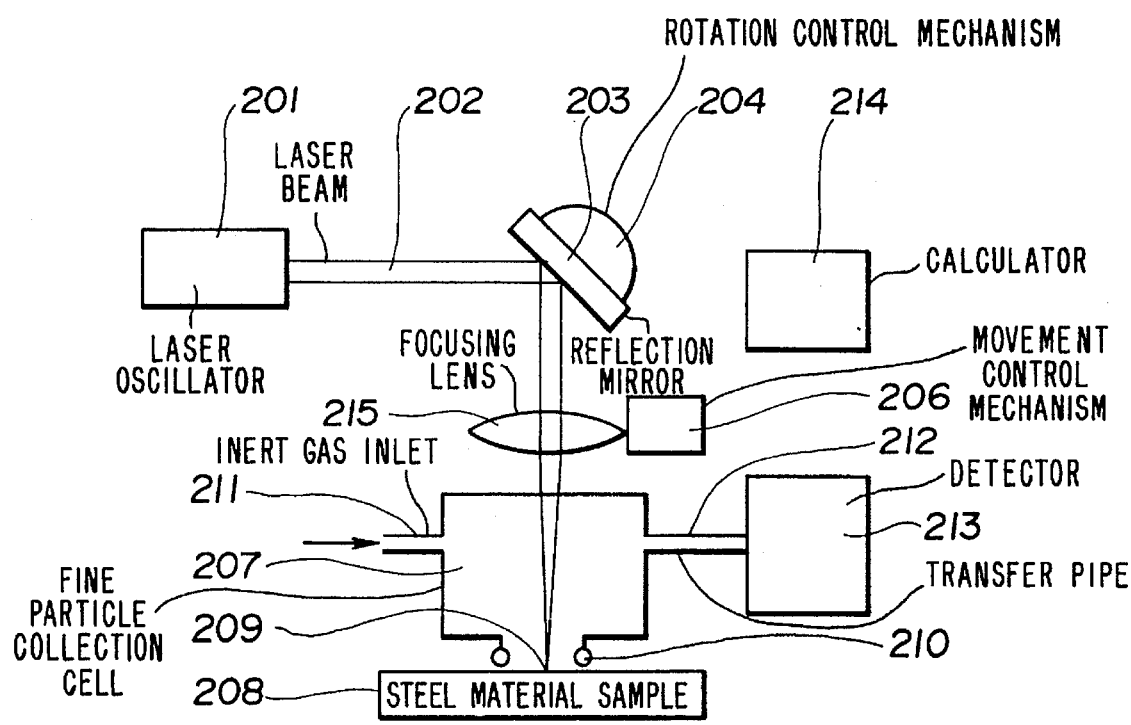
FIG. 8 is a schematic view illustrating an apparatus which is used for a method for analyzing steel according to an Embodiment-3 of the present invention.

FIG. 8 shows a schematic view illustrating an apparatus for conducting a method of the present invention. A propagation route for a laser beam 202 emitted from a laser oscillator 201 is defined by a reflection mirror 203. The reflection mirror is provided with a rotation control mechanism 204 to control the beam propagation route. The reflected laser beam 202 is converged by a focusing lens 205. The focusing lens 215 has a parallel movement control mechanism 206 to control the parallel movement. The converged laser light 202 passes through the fine particle collection cell 207 to converge on the surface of the steel material sample 208 to form a focusing point and to form a laser beam irradiating spot 209. The fine particle collection cell 207 has an opening which contacts the surface of the sample via a sealing material 210. An inert gas is introduced from the inert gas inlet 211 to make the inside space an inert gas atmosphere. The inert gas transfers the fine particles generated in the fine particle collection cell to the detector 213 through the transfer piping 212, where the analysis of the fine particles is conducted.

The rotation control mechanism 204 and the parallel movement control mechanism 206 receive the command of control mode instructed by a calculator 214. The calculator 214 receives the information of depth, width, and length of the analytical line, locus of irradiating spot, half width value and peak output of pulse laser, calculates the rotational speed, the maximum rotational angle, rotational frequency, quantity of parallel movement and moving speed of focusing lens, and generates a command for controlling to the rotation control mechanism 204 and the parallel movement control mechanism 206. Using an apparatus illustrated in FIG. 8, a linear analysis of a cold-rolled sheet and a hot dip zincing steel sheet (preprared by CGL which means a continuous galvanizing line) was carried out in respect of their surface abnormality zone. The causes were identified.

The laser oscillator used a YAG laser with Q switch, and oscillated at a frequency range of from 100 to 5000 Hz. The detector used a high frequency induction associated plasma emission spectral analyzer. On the laser incidence face of the fine particle collection cell, a transmission window made by quartz glass was provided, and a rubber "0" ring was applied as the sealing material. The rotation of the reflection mirror was carried out by a step motor to form a mechanism for repeating forward rotation and reverse rotation at a specified angle. The parallel movement of focusing lens is done by a mechanism which converts the rotational motion of the step motor to a straight line motion while repeating the traverse at a length of the analytical line.

In the case that the irradiating spot was to be moved in a zig-zag mode, either one of the loci of a Z-shaped one where both the lengthwise movement along the analytical line and the width-wise movement were applied at a time or a U-shaped one where only one of the lengthwise movement and the lateral movement was applied, and the selected locus was entered the calculator. Based on the length of the analytical line, the calculator determined the distance of parallel movement of the focusing lens. Also the calculator determined the maximum rotational angle of the reflection mirror by dividing the width of the analytical line by the distance between the reflection mirror and the focusing lens. Furthermore, the calculator computed the necessary moving speed of the irradiating spot and the necessary reciprocating rotational speed of the reflection mirror from the depth of the analytical line depending on the peak output.

The comparison of component concentrations was carried out based on the emission intensity of elements measured by ICP.

Table 6 shows the detailed conditions for analysis. FIG. 11 through 15 show the analytical results, and Table 7 shows the evaluation result based on the analytical result compared with the result of prior art emission spectra method.

FIG. 11 through FIG. 15 show the analytical result on the sample A through E. Vertical axis shows the analytical value represented by Fe intensity ratio. Horizontal axis shws the distance of movement of analytical point along the analytical line. The position of abnormal zone is pointed with arrow mark.

Figure 11:
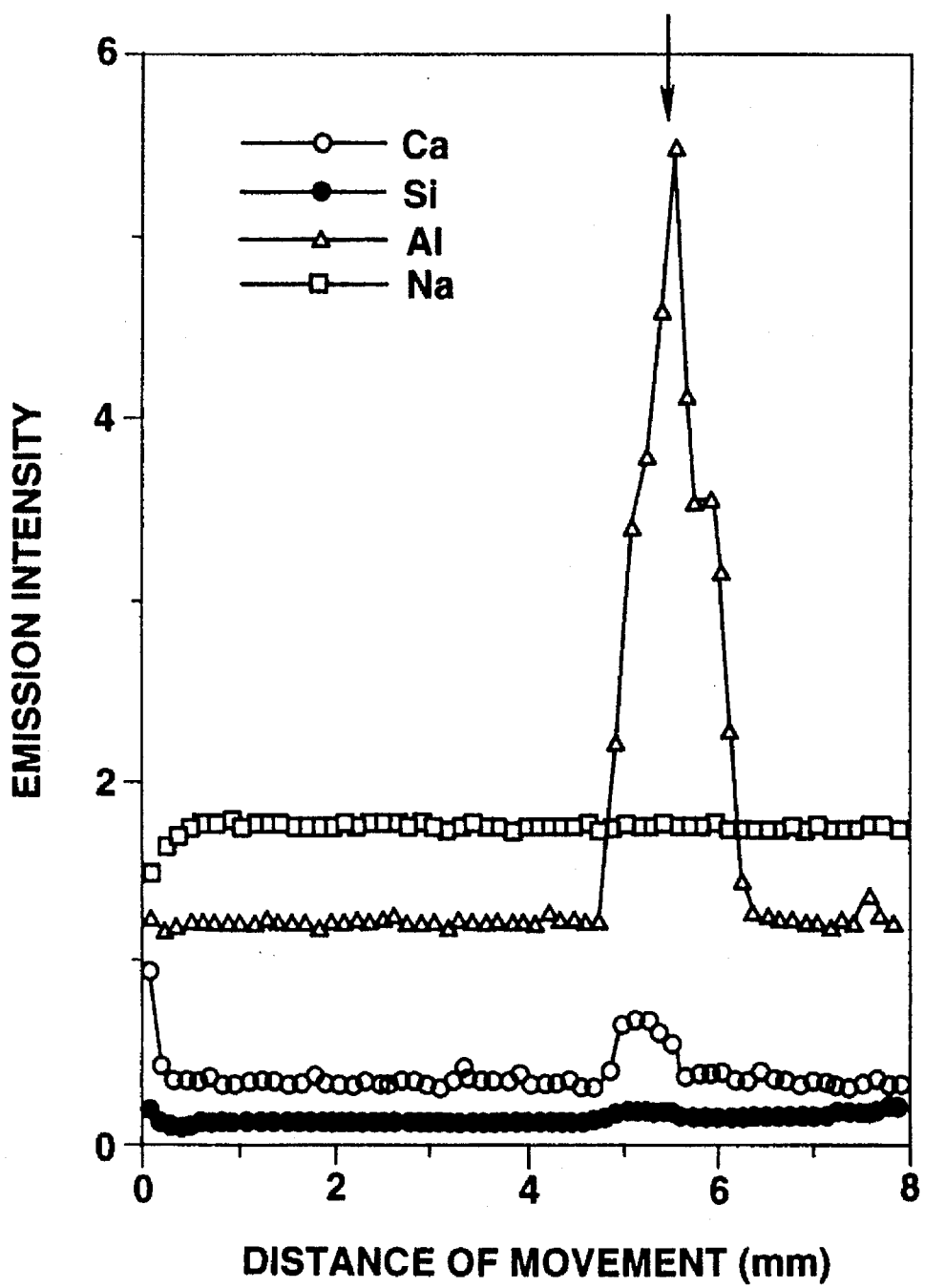
FIG. 11 is a graphic representation showing a relation between a distance of movement of an analytical point on an analytical line and a Fe intensity ratio according to the Embodiment-3 of the present invention.
Figure 12:
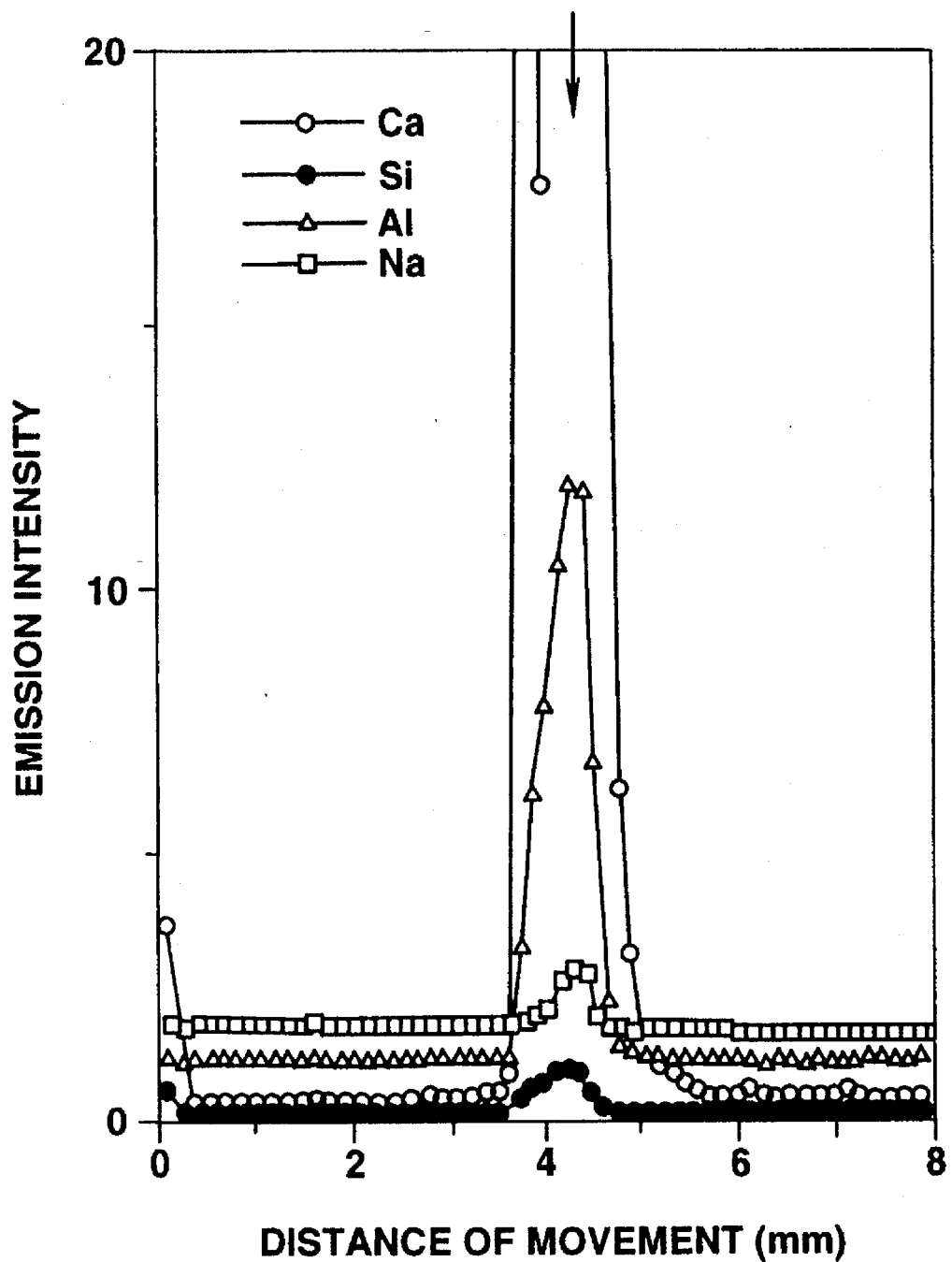
FIG. 12 is another graphic representation showing a relation between a distance of movement of an analytical point on an analytical line and a Fe intensity ratio according to the Embodiment-3 of the present invention.
Figure 13:
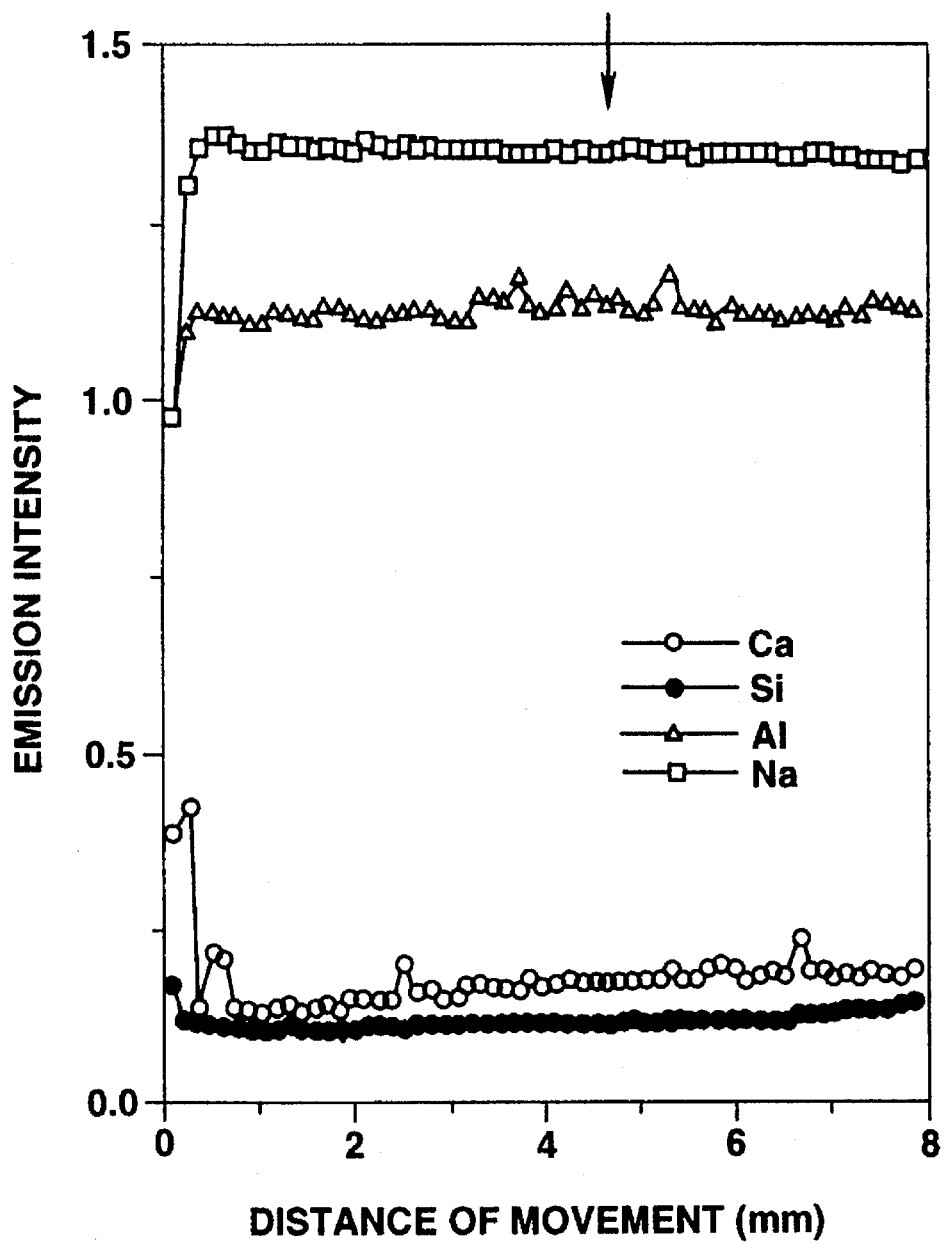
FIG. 13 is further another graphic representation showing a relation between a distance of movement of an analytical point on analytical line and a Fe intensity ratio according to the Embodiment-3 of the present invention.
Figure 14:
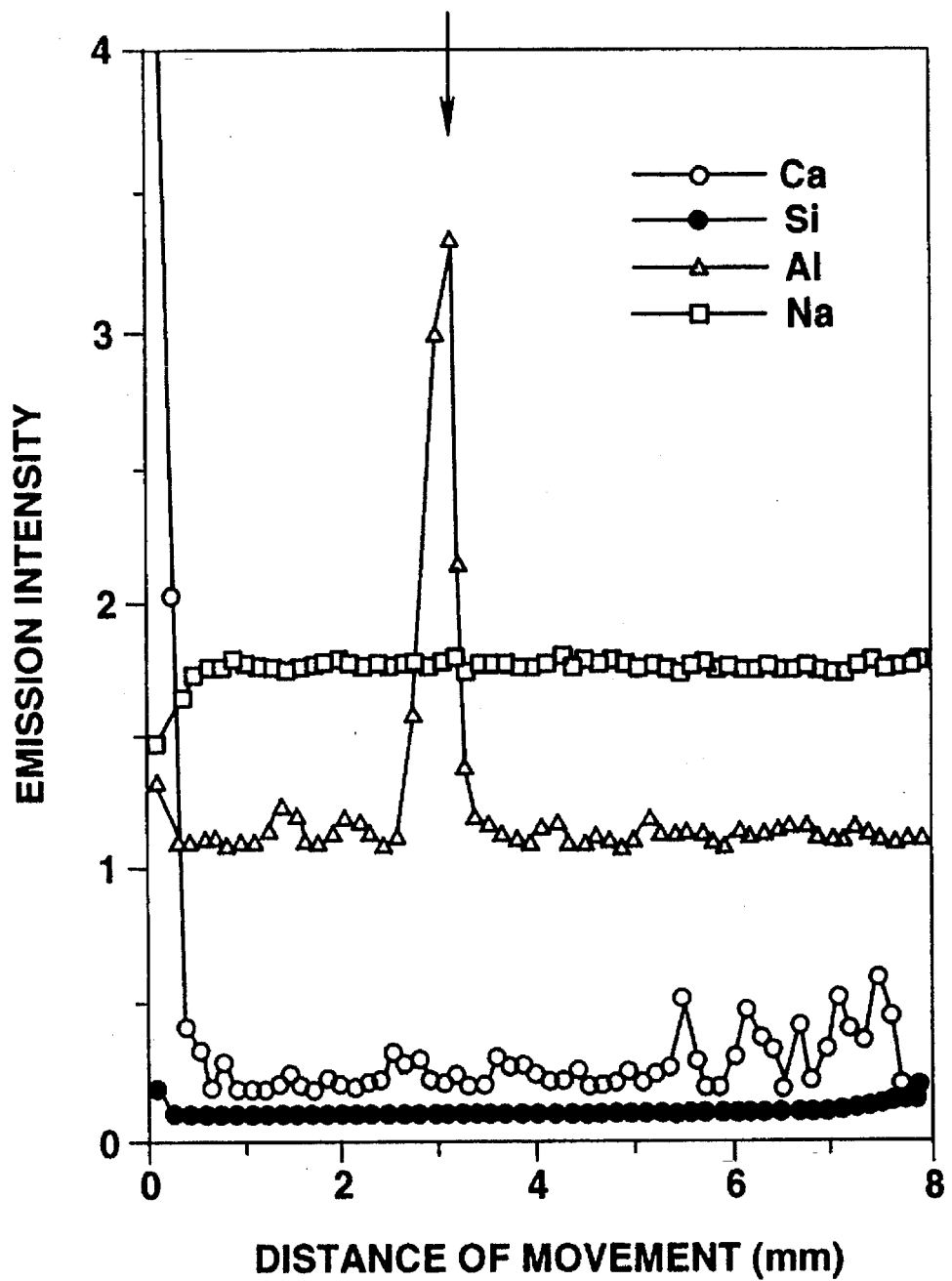
FIG. 14 is still further another graphic representation showing a relation between a distance of movement of an analytical point on an analytical line and a Fe intensity ratio according to the Embodiment-8 of the present invention.
Figure 15:
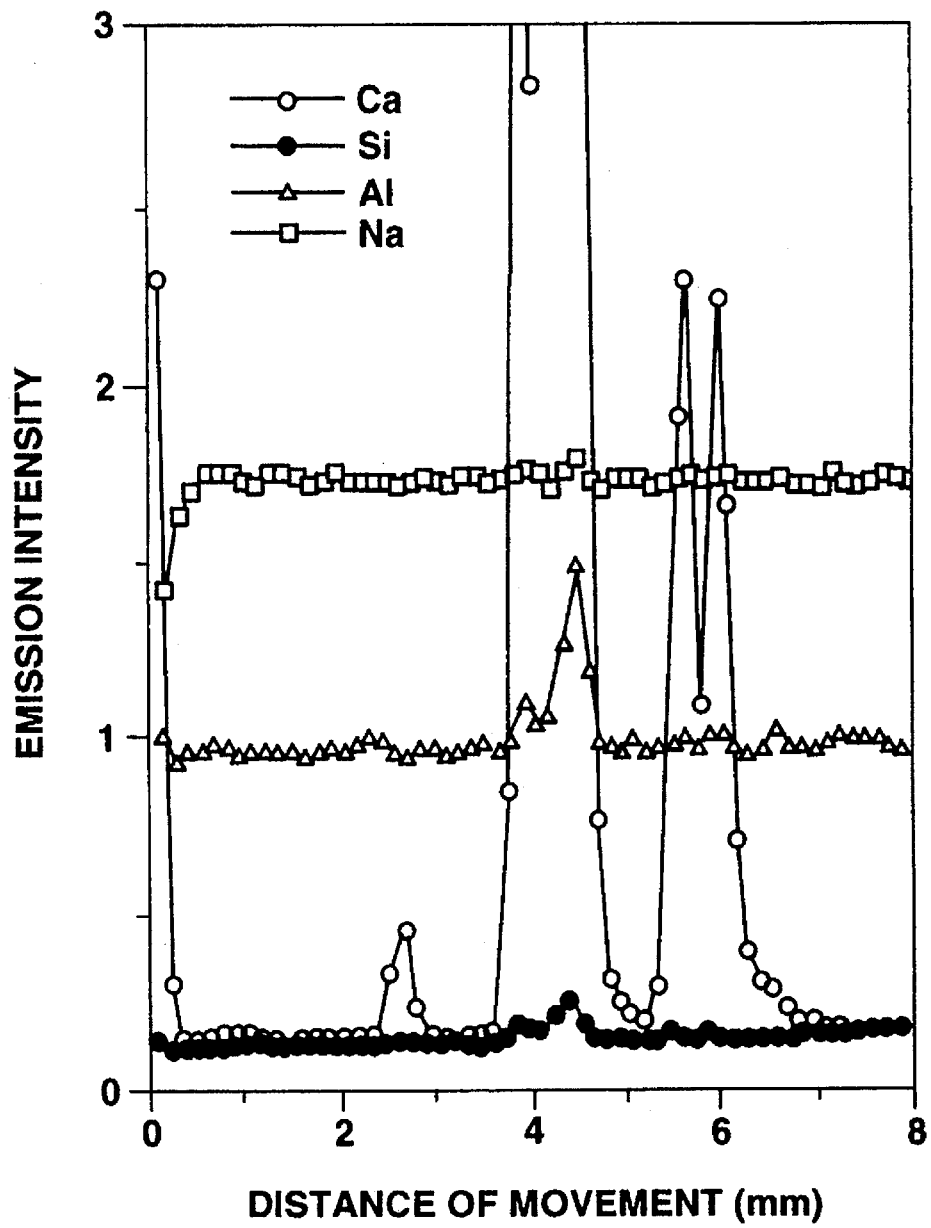
FIG. 15 is still furthermore another graphic representation showing a relation between a distance of movement of an analytical point on an analytical line and a Fe intensity ratio according to the Embodiment-3 of the present invention.

In FIG. 11, when the analytical line came in an abnormal zone, Al content showed a sudden rise, and Ca content gave an increase to some degree. Similarly in FIG. 12, Ca, Al, Na, and Si content increased at the abnormal zone. FIG. 15 shows the increase of Al, FIG. 8 shows the increase of Ca and Al in the abnormal zone. However, FIG. 13 does not show any fluctuation of components.

When the results given in FIG. 11 through FIG. 15 were summarized and when the summarized result was compared with the results of prior art emission spectral analysis, the sample A gave a detection of Ca in Example of the invention, while Ca did not detected by the prior art example. Also for the sample B, the prior art example did not detect Na, which might induced a false evaluation on causes. According to an Example of the invention, the samples D and E where the analysis was carried out down to 50 μm and to 100 μm, a varied composition beneath the coating layer was detected. Therefore, the cause of abnormality was defined as the alumina inclusions and the inclusions of a composite compound of oxide calcium-aluminum. Nevertheless, the conventional example gave no detection of fluctuating component, and the cause of abnormality presumably comes from scale.

As described in detail above, the present invention uses a laser gasification method for the analysis to identify the causes of an abnormality on the steel surface, so the component detection is possible even when the abnormal zone is covered with an insulation material. In addition, the control of laser irradiating condition easily changes the depth and width of the analytical line, and the overlooking of the composition at an abnormal section is difficult to occur.

TABLE 6

| Sample | Steel Material | Half Width of Pulse (μm) | Peak Output (kW) | Locus of Irradiating spot | Analytical Line | | |
|---|---|---|---|---|---|---|---|
| | | | | | Depth (μm) | Length (mm) | Width (mm) |
| A | Cold-rolled Material | 0.5 | 20 | Z-shape | 20 | 8 | 1 |
| B | Cold-rolled Material | 0.1 | 100 | Z-shape | 50 | 8 | 1 |
| C | Cold-rolled Material | 0.02 | 1000 | U-shape | 20 | 8 | 2 |
| D | CGL | 0.1 | 500 | Straight Line | 100 | 8 | — |
| E | CGL | 0.1 | 200 | U-shape | 50 | 8 | 2 |

TABLE 7

| | | Example | | Conventional Example | |
|---|---|---|---|---|---|
| Sample | Type of Steel | Element Detected in Abnormal Zone | Cause | Element Detected in Abnormal Zone | Cause |
| A | Cold-rolled Material | Less Al, Ca | Alumina | Al | Alumina |
| B | Cold-rolled Material | Ca, Si, Al, Na | Powder | Ca, Si, Al | Inclusions |
| C | Cold-rolled Material | None | Scale | None | Scale |
| D | CGL | Al | Alumina | None | Scale |
| E | CGL | Ca, Al | Inclusions | None | Scale |

What is claimed is:

1. A method for analyzing steel comprising the steps of:
   (a) a first grinding step of mechanically grinding a surface of a steel ingot to form an analysis area on the steel ingot;
   (b) bringing a sealing section of a cell into contact with the analysis area to seal the analysis area, said cell having the sealing section at an opening end thereof;
   (c) a second grinding step of further grinding the analysis area to remove soil adhered on a surface layer and an oxide layer generated in the surface layer of the steel ingot, while an inert gas is introduced into an inside of the cell;
   (d) charging a pulsed energy of $10^8$ W/cm$^2$ or more onto the area for analysis to generate fine particles; and
   (e) transferring the fine particles by using the inert gas introduced into the inside of the cell to cause an excitation flame for an excitation analysis.

2. The method of claim 1, wherein said second grinding step is carried out by a mechanical grinding.

3. The method of claim 1, wherein said second grinding step is carried out by a spark discharge.

4. The method of claim 1, wherein said second grinding step is carried out by a pulse direct-current discharge.

5. The method of claim 1, wherein said second grinding step is carried out by a pulsed laser beam.

6. The method of claim 5, wherein said second grinding step is carried out by a sweep irradiation of the laser beam with an oscillation frequency of 1 kHz or more and an energy density of $10^8$ to $10^{11}$ cm$^2$, the laser beam being irradiated on the analysis area in an irradiation spot at least 10 times while moving the irradiation spot in an area range of at least 1 mm$^2$.

7. The method of claim 1, wherein said inert gas of the second grinding step is argon gas.

8. The method of claim 7, wherein said argon gas is a purified argon gas by an argon gas purifier, the purified argon gas having a carbon content of 1 μg/liter or less.

9. The method of claim 1, wherein said step of charging the pulsed energy to generate the fine particles is carried out by irradiating a laser beam with an oscillation frequency of 100 Hz or more and an energy density of $10^8$ to $10^8$ W/cm$^{11}$ cm$^2$ on the area for analysis in an irradiating spot while moving the irradating spot at least 1 mm$^2$.

10. The method of claim 1, wherein said excitation analysis is carried out by an atomic absorption analysis and the excitation flame is an acetylene combusted flame.

11. The method of claim 1, wherein said excitation analysis is carried out by a plasma emission analysis and the excitation flame is an argon plasma flame.

12. The method of claim 1, wherein said excitation analysis is carried out by a plasma emission analysis and the excitation flame is an inductively coupled plasma flame.

13. The method of claim 9, wherein said inert gas of the second grinding step is argon gas having a carbon content of 1 µg/liter or less.

14. An apparatus for analyzing steel comprising:
   (a) a first grinding means for mechanically grinding a surface of a steel ingot to form an analysis area;
   (b) a cell having a sealing section at an opening end thereof, said sealing section being in contact with the analysis area;
   (c) said cell having a gas inlet and a gas outlet at both sides thereof, an inert gas being introduced through the gas inlet and the inert gas being discharged through the gas outlet;
   (d) a second grinding means for further grinding the analysis area to remove soil adhered on a surface layer and an oxide layer generated in the surface layer of the steel ingot, while the inert gas is into an inside of the cell through the gas inlet;
   (e) energy charging means for charging a pulsed energy on the analysis area to generate fine particles; and
   (f) an excitation analyzer for analyzing the fine particles which are transferred through the gas outlet of the cell.

15. The apparatus of claim 14, wherein said first grinding means is a grinder.

16. The apparatus of claim 14, wherein said second grinding means is a grinding device using a pulsed laser beam.

17. The apparatus of claim 14, wherein said energy charging means is a pulsed laser irradiation device.

18. The apparatus of claim 17, wherein said pulsed laser irradiation device comprises an oscillator, a reflection mirror, a single-focus focusing lens and a control device for controlling an irradiating spot, said control device controlling a reflection angle by rotating the reflection mirror or said control device controlling a parallel movement of the single-focus focusing lens.

19. The apparatus of claim 14, wherein said excitation analyzer is an atomic absorption analyzer.

20. The apparatus of claim 14, wherein said excitation analyzer is a plasma emission analyzer.

21. The apparatus of claim 18, wherein said first grinding means is a grinder and said second grinding means is a grinding device employing a pulsed laser beam.

22. A method for analyzing steel comprising the steps of:
   (a) preparing a sample by sampling a molten steel and solidifying the molten steel;
   (b) putting the sample into a sample chamber under an inert gas atmosphere, the sample being at a red hot state;
   (c) irradiating a pulsed laser beam on a surface of the sample in the sample chamber to generate fine particles, the fine particles generated from a depth of 25 µm or more under the surface being a specimen for composition analysis;
   (d) transferring the fine particles to an an inductively coupled plasma analyzer; and
   (e) analyzing a composition of the fine particles by the inductively coupled plasma analyzer.

23. The method of claim 22, wherein said inert gas atmosphere of the sample chamber is an argon gas atmosphere, the argon gas having a carbon content of 1 g/liter or less.

24. The method of claim 22, wherein said pulsed laser beam is irradiated with an oscillation frequency of 100 Hz or more and an energy density of $10^8$ to $10^{11}$ W/cm$^2$ at an irradiating spot while moving the irradiating spot.

25. The method of claim 23 wherein said pulsed laser beam is irradiated with an oscillation frequency of 100 Hz or more and an energy destiny of $10^8$ to $10^{11}$ W/cm on an irradiating spot while moving the irradiating spot.

26. An apparatus for analyzing steel comprising:
   (a) a sample chamber for a sample, said sample chamber comprising an analytical cell section, a sample holding section and an exposure hole for connecting the sample holding section with the analytical cell section, the sample being received in the sample holding section;
   (b) the sample holding section having an inner surface in contact with a surface of the sample and the inner surface having a substantially same curved surface as that of the sample;
   (c) a laser oscillator for irradiating a pulsed laser beam to generate fine particles, the pulsed laser beam being irradiated on the sample through the analytical cell section and the exposure hole;
   (d) transfer means for transferring the fine particles to an outside of the analytical cell section by introducing an inert gas into the analytical cell section; and
   (e) an inductively coupled plasma analyzer for analyzing a composition of the transferred fine particles.

27. The apparatus of claim 26, wherein said transfer means includes a carrier gas piping which connects the sample chamber with the inductively coupled plasma analyzer.

28. The apparatus of claim 27, wherein said carrier gas piping is a metallic piping.

29. The apparatus of claim 27, wherein said carrier gas piping is a glass piping.

30. A method for analyzing steel comprising the steps of:
   (a) irradiating a pulsed laser beam on a spot on a steel surface to generate fine particles, the pulsed laser beam having a pulse half width of 0.02 to 0.5 µsec and a pulse peak output of 20 kW to 5 Mw;
   (b) moving the spot on the steel surface so that a zig-zag movement is performed;
   (c) transferring the generated fine particles to a detector by an inert gas; and
   (d) analyzing a composition of the fine particles by the detector, wherein an abnormal zone of the steel being detected by a transition of the composition.

31. The method of claim 30, wherein the zig-zag movement is carried out by combining a rotation of a reflection mirror and a parallel movement of a focusing lens.

* * * * *